(12) United States Patent
Weiser et al.

(10) Patent No.: US 8,104,958 B2
(45) Date of Patent: Jan. 31, 2012

(54) ASSIGNING X-RAY MARKERS TO IMAGE MARKERS IMAGED IN THE X-RAY IMAGE

(75) Inventors: Manfred Weiser, München (DE); Rupert Heigl, München (DE)

(73) Assignee: Brainlab AG, Feldkirchen (DE)

( * ) Notice: Subject to any disclaimer, the term of this patent is extended or adjusted under 35 U.S.C. 154(b) by 173 days.

(21) Appl. No.: 12/545,104

(22) Filed: Aug. 21, 2009

(65) Prior Publication Data

US 2010/0046718 A1 Feb. 25, 2010

Related U.S. Application Data

(60) Provisional application No. 61/111,018, filed on Nov. 4, 2008.

(30) Foreign Application Priority Data

Aug. 22, 2008 (EP) .................................. 08162808

(51) Int. Cl.
*G01D 18/00* (2006.01)
*G06K 9/20* (2006.01)

(52) U.S. Cl. ........ 378/207; 378/162; 378/204; 382/132; 600/426

(58) Field of Classification Search .................. 378/162, 378/164, 165, 207, 204; 600/426, 429; 382/132
See application file for complete search history.

(56) References Cited

U.S. PATENT DOCUMENTS

| | | | | |
|---|---|---|---|---|
| 6,044,132 A * | 3/2000 | Navab | | 378/163 |
| 6,081,577 A * | 6/2000 | Webber | | 378/23 |
| 6,359,960 B1 * | 3/2002 | Wahl et al. | | 378/20 |
| 6,428,547 B1 * | 8/2002 | Vilsmeier et al. | | 606/130 |
| 6,527,443 B1 * | 3/2003 | Vilsmeier et al. | | 378/205 |
| 6,585,412 B2 * | 7/2003 | Mitschke | | 378/207 |
| 6,725,082 B2 * | 4/2004 | Sati et al. | | 600/429 |
| 6,851,855 B2 * | 2/2005 | Mitschke et al. | | 378/207 |
| 6,932,506 B2 * | 8/2005 | Mitschke et al. | | 378/207 |
| 7,010,095 B2 * | 3/2006 | Mitschke et al. | | 378/162 |
| 7,016,456 B2 * | 3/2006 | Basu et al. | | 378/18 |
| 7,147,373 B2 * | 12/2006 | Cho et al. | | 378/207 |
| 7,241,045 B2 * | 7/2007 | Skalli et al. | | 378/207 |
| 7,547,307 B2 * | 6/2009 | Carson et al. | | 606/88 |
| 7,907,699 B2 * | 3/2011 | Long et al. | | 378/65 |

(Continued)

FOREIGN PATENT DOCUMENTS

DE 197 03 556 8/1998

(Continued)

OTHER PUBLICATIONS

Bernhard E. H. Claus, "Geometry Calibration Phantom Design for 3D Imaging," Medical Imaging 2006: Physics of Medical Imaging, Proceedings of SPIE vol. 6142, 61422E (2006).*

(Continued)

*Primary Examiner* — Allen C. Ho
(74) *Attorney, Agent, or Firm* — Renner, Otto, Boisselle & Sklar, LLP

(57) ABSTRACT

The present application relates to an x-ray marker device comprising an arrangement of x-ray markers, wherein the arrangement defines straight lines which are referred to as device straight lines, wherein at least some of the device straight lines, which are referred to as pyramid straight lines, comprise portions which define edges of at least one pyramid.

15 Claims, 8 Drawing Sheets

U.S. PATENT DOCUMENTS

| | | | |
|---|---|---|---|
| 7,922,391 B2 * | 4/2011 | Essenreiter et al. | 378/207 |
| 2005/0109855 A1 | 5/2005 | McCombs | |
| 2005/0113682 A1 | 5/2005 | Webber et al. | |
| 2007/0122020 A1 * | 5/2007 | Claus et al. | 382/131 |

FOREIGN PATENT DOCUMENTS

| | | |
|---|---|---|
| DE | 199 17 867 | 11/2000 |
| DE | 102 15 808 | 11/2003 |
| EP | 0 853 920 | 7/1998 |

OTHER PUBLICATIONS

Schönherr et al., "Ein neues algorithmisches Verfahren zur Fluoroskopie-basierten Neuronavigation", 2004, [Online] http://sunsite.informatik.rwth-aachen.de/Publications/CEUR-WS/vol-116/p229.pdf.

Sorensen et al., "Image-Guided Radiotherapy Using a Mobile Kilovoltage X-Ray Device", 2006, Medical Dosimetry, pp. 40-50.

Yaniv et al., "Fluoroscopic Image Processing for Computer-Aided Orthopaedic Surgery", 1998, MICCAI' 98 LNCS, pp. 325-334.

* cited by examiner

ASSIGNING X-RAY MARKERS TO IMAGE MARKERS IMAGED IN THE X-RAY IMAGE

RELATED APPLICATION DATA

This application claims the priority of U.S. Provisional Application No. 61/111,018, filed on Nov. 4, 2008, which is hereby incorporated in its entirety by reference.

FIELD OF THE INVENTION

The present invention relates to assigning x-ray markers to images of said x-ray markers. The images of the x-ray markers are referred to here as image markers.

BACKGROUND OF THE INVENTION

Known examples of x-ray marker devices include registration bodies, so-called fluoroscopic registration kits. These are fixedly connected to the image intensifier of a C-arm. Some enable a rotation relative to the image intensifier. Optical markers (navigation markers) are also attached to the registration bodies and allow the position of the registration body to be determined by means of a navigation system. The navigation systems are used for so-called image-guided navigation (image-guided surgery). The optical markers are for example detected by means of cameras which are components of the navigation system. Evaluating an x-ray image and the x-ray markers imaged in it and knowing the position of the registration body relative to the x-ray apparatus allow an instrument to be registered in a desired reference system which can be predetermined by the navigation system and allow the instrument to be displayed virtually in the x-ray image, without taking an x-ray recording.

The following documents relate to such methods or devices: U.S. 61/054,187; DE 199 17 867 A1.

If the registration body can be rotated, then there are only the options of rotating and mirroring when evaluating the x-ray image in order to achieve an assignment between the image markers and the x-ray markers. The option of mirroring is available since the x-ray image can be output in a mirrored or non-mirrored form by the x-ray apparatus. Due to this low number of possible variations (rotating and mirroring), an assignment is obvious. An assignment between the x-ray markers and the image markers can thus be performed simply and quickly by means of an algorithm.

For the assignment, information concerning the x-ray beam imaging geometry is then for example determined in accordance with the principles of the pinhole camera. This information in particular allows the position of an x-ray source to be calculated relative to the registration body.

The x-ray beam imaging geometry can for example be defined via a spatial transformation into a centre of projection (six external imaging parameters: three rotational, three translational; and four internal imaging parameters: two scaling factors which convert global coordinates [mm] into pixels of the electronic image, and the coordinates of the (computational) principal point).

The principle described above also applies in principle to the scout view (see further below). With respect to the principal point, the two coordinates (u, v) are preferably taken as the calculated centre point of the image.

The data which contains the above information concerning the x-ray beam imaging geometry is referred to here as the imaging geometry data. The imaging geometry data in particular comprises the calculated projection matrix. The imaging geometry data, and in particular the projection matrix, represent a general law of imaging for the given x-ray beam imaging geometry. They thus allow a calculation of how an arbitrary point in space will be displayed in the (undistorted) x-ray image, assuming the same x-ray beam imaging geometry as obtained when the x-ray image—which displays an image of the x-ray marker device—was produced. It thus represents a generalization of the imaging process which assumes the specific scenario of imaging the x-ray marker device onto the x-ray image with a given x-ray beam imaging geometry.

Imaging geometry data is for example calculated by means of using a camera model which reflects the actual imaging characteristics as well as possible. The usual camera model is the pinhole camera model, i.e. the imaging geometry data is for example calculated on the basis of the principles of the pinhole camera. Reference is made in this respect to the following publications, which are hereby incorporated into the disclosure by reference:

1. "An Efficient and Accurate Camera Calibration Technique for 3D Machine Vision", Roger Y. Tsai, Proceedings of IEEE Conference on Computer Vision and Pattern Recognition. Miami Beach, Fla., 1986, pages 364-374.
2. "A Versatile Camera Calibration Technique for High-Accuracy 3D Machine Vision Metrology Using Off-the-shelf TV Cameras and Lenses", Roger Y. Tsai, IEEE Journal of Robotics and Automation, Volume RA-3, No. 4, August 1987, pages 323-344. See also at http://www.cs.cmu.edu/~rgw/TsaiDesc.html
3. Publication by Ziv Yaniv, "Fluoroscopic X-ray Image Processing and Registration for Computer-Aided Orthopedic Surgery".

As may be gathered from citation No. 2 given above and the accompanying internet address, five internal imaging parameters are mentioned in the "Tsai's Camera Model" described in said document, and are referred to in said document as "internal parameters". However, only four internal imaging parameters were mentioned above. This is due to the fact that an undistorted image is assumed in the given scenario, and the parameter "kappa1" is therefore not required. If the image were to be distorted, a rectification would preferably have to be performed beforehand (see also discussion further below). In general, the internal imaging parameters describe how the camera, i.e. the x-ray apparatus in the given scenario, forms an image, while the external parameters describe the position of the x-ray apparatus (its location and orientation) in the global coordinate system. In accordance with the invention, the Tsai Camera Model is adapted to the particular conditions of the x-ray beam imaging, as described in particular in the publication by Ziv Yaniv (see above). The two scaling factors f and/or 1/f and sx can in particular be used.

If the imaging geometry data has been determined, it is then possible to check, using a virtual x-ray image of the registration body, whether the assignment is correct. The virtual x-ray image is determined by the imaging geometry data.

If, however, the relative position between the image intensifier and the registration body is unknown, then there are a greater number of possible assignments between the x-ray markers and the image markers, which can lead to a significant computing time of a number of minutes or hours (depending on the number of markers). In daily practice, however, such a period of computation is unacceptable. Due to this long computing time, registration bodies are in practice currently mounted fixedly relative to the image intensifier.

Another example of x-ray marker devices is "x-ray calibration phantoms" (cf. DE 102 15 808) or "x-ray grids" (cf. EP 08 156 293.6 or U.S. 61/054,187) which can be used to determine calibration information for calibrating a 3D CT x-ray apparatus, in particular used to determine the position of a 3D x-ray measurement volume relative to a reference system which is predetermined by the navigation system. The x-ray marker devices, in particular the support (for example, side walls) for the x-ray markers, and the x-ray markers can be optically opaque.

SUMMARY OF THE INVENTION

It is an object of the invention to facilitate the assignment of x-ray markers to image markers even when there is no information concerning the position of the x-ray marker device relative to the x-ray apparatus, in particular relative to the x-ray source and the image intensifier.

The above object is solved by the subjects of the independent claims. The dependent claims are directed to advantageous developments.

An x-ray marker device in accordance with the invention preferably comprises x-ray markers. The arrangement of the x-ray markers preferably defines at least two straight lines, i.e. the position of the x-ray markers (for example, the geometric centre point of the x-ray markers) defines points, wherein at least two of these points respectively define straight lines. These straight lines are referred to here as "device straight lines" in order to distinguish them from the straight lines which are defined in the x-ray image, which are mentioned below and referred to as "image straight lines". At least some of the device straight lines comprises portions which match the edges, in particular the side edges, of a (at least one) pyramid, i.e. the portions define the edges of a (at least one) pyramid. In particular, the intersection point ("device intersection point") of at least two straight lines defines at least one pyramid tip. The pyramid tip, together with a (at least one) x-ray marker, can also define a (at least one) device straight line (more specifically, a (at least one) "pyramid straight line").

The straight lines and pyramids can in particular be virtual (geometric) constructs which are defined by the physical (actual and material) x-ray markers.

Device straight lines which comprise portions which define edges of a pyramid are referred to here as "pyramid straight lines".

Since both the device straight lines and the pyramid straight lines are straight lines, they are invariant when linearly imaged. Examples of linear images include projective images, perspective projections, parallel projections and the so-called "scout view" (a mixture of parallel projections and perspective projections). Common x-ray recordings are usually perspective projections. The aforesaid scout view is often predominant in modern CT scanners. A parallel projection is also ultimately possible if a punctiform x-ray source and the detector move in parallel over the patient. The present invention in particular uses the linear imaging characteristics of x-ray imaging. Where projective imaging is mentioned in the following, this is purely by way of example. The x-ray marker device in accordance with the invention thus has an arrangement which exhibits an invariant characteristic. Since the arrangement in accordance with the invention defines pyramid straight lines, this invariant characteristic is easier to locate in the x-ray image, and the assignment between the x-ray markers and the image markers is facilitated, as explained below.

The aforesaid pyramid straight lines are defined by straight line forming points which in turn result from the arrangement of the x-ray markers. In accordance with the laws of geometry, at least two points—i.e. straight line forming points— are needed in order to define a straight line. The straight line forming points are in particular determined by the position of the x-ray markers, i.e. for example by the respective geometric centre point of the x-ray markers (i.e. for example the centre point of a sphere, if the x-ray markers are spherical). Straight line forming points can also be intersection points which result from device straight lines which are in turn defined by straight line forming points, which are x-ray markers. If, for example, at least two x-ray markers respectively lie on the edges of a pyramid, the pyramid straight lines intersect in a device intersection point. This device intersection point likewise represents a straight line forming point which— together with another x-ray marker which for example lies at a corner of the pyramid—can form another pyramid straight line which by its nature likewise passes through the same pyramid tip but is not identical to the other two aforementioned pyramid straight lines.

The x-ray markers which define straight line forming points of a pyramid straight line can lie on both sides of the pyramid tip. Preferably, however, more x-ray markers lie on one side than on the other side as viewed from the pyramid tip, at least in the case of one pyramid straight line. In particular, the x-ray markers preferably lie on one side only and not on the other. This preferably applies to at least one of the pyramid straight lines, particularly preferably to at least two of the pyramid straight lines and even more preferably to at least three of the pyramid straight lines or to all of the pyramid straight lines. This can subsequently facilitate the assignment between the x-ray markers and the image markers, since the proximity relationships—i.e. the order starting from the device intersection point (the pyramid tip)—can be used. This is explained in even more detail below.

X-ray markers are in particular bodies made of a material which is impermeable to the x-ray beams or at least significantly attenuates them. The bodies can be shaped in any way and can in particular assume basic geometric shapes such as spheres or cuboids. The bodies are in particular distanced from each other. The distance is in particular greater than the body diameter of the x-ray markers. The body diameters are preferably greater than 1 mm and/or smaller than 3 cm.

The x-ray marker device preferably comprises at least five x-ray markers, wherein at least four of the at least five x-ray markers define two pyramid straight lines which intersect in a pyramid tip. At least one other x-ray marker, together with the pyramid tip, forms another pyramid straight line.

At least two x-ray markers are preferably situated on each of at least three of the pyramid straight lines, in order to subsequently be able to better identify artifacts in the x-ray image. The pyramid tip is preferably situated outside the region in which the x-ray markers are situated. In particular, no x-ray marker lies on the pyramid tip in this case.

The aforesaid straight lines, in particular the device straight lines and pyramid straight lines, are invariant in projective imaging. The arrangement of the x-ray markers in accordance with the invention thus describes an invariant characteristic.

Invariant characteristics are characteristics which are retained in projective imaging. In particular, these characteristics are invariants of each projective image. In particular, they represent a characterizing feature of the projective geometry. Invariant characteristics of the projective geometry include for example straight lines which are defined by the arrangement of the x-ray markers, such as for example the device straight lines, and which are also referred to here as "invariant straight lines". Another example is the so-called cross-ratio, which likewise represents an invariant characteristic, i.e. an invariant of the projective image. In geometry, the cross-ratio is a number which characterizes the reciprocal position of four different points on a straight line, wherein two of these points determine a path which is divided by the other two points. The cross-ratio is defined as the ratio of the two partial ratios.

The x-ray marker device defines in particular at least six straight line forming points. These at least six straight line forming points are preferably determined from x-ray markers. In particular, one of the at least six straight line forming points can also be a device intersection point, in particular a pyramid tip, at which in particular no x-ray marker is situated. The at least six straight line forming points preferably do not all lie in one plane.

The total number of x-ray markers is in particular smaller than 30 or 20 or 10. The maximum distance between any two x-ray markers of the x-ray marker device is in particular smaller than the diameter of a detection range of an x-ray apparatus, in particular smaller than 50 cm or 30 cm or 20 cm or 10 cm.

Preferably, at least six of the x-ray markers lie on invariant straight lines. They are also referred to here as invariant x-ray markers, since they define an invariant characteristic.

Preferably, at least three of the pyramid straight lines each contain a portion which respectively corresponds to a side edge of the same pyramid. Preferably, at least three of the pyramid straight lines have portions which respectively correspond to both a side edge of one pyramid and the base edge of at least one other pyramid, in particular the base edges of two other pyramids. Preferably, all the x-ray markers lie on pyramid straight lines.

As mentioned, the straight line forming points can also be device intersection points. Device intersection points fulfill at least the condition that at least two device straight lines intersect in them. A device intersection point can coincide with the position of an x-ray marker or can also result at a point in space at which no x-ray marker is situated but at which at least two device straight lines still intersect. Preferably, an intersection point is only a device intersection point if a particular, predetermined number of device straight lines intersect in it and/or the number is greater than or equal to a predetermined minimum number (for example three, four or five) and/or smaller than or equal to a predetermined maximum number (for example, the total number of x-ray markers of the x-ray marker device minus 1 or 2). The predetermined number is preferably at least three. The predetermined number can be the same for all the device intersection points or can be different. Using the predetermined number, the minimum number or the maximum number, artifacts can be more easily identified.

Preferably, at least six of the x-ray markers lie on device straight lines, i.e. are in particular straight line forming points. Preferably, at least three straight line forming points lie on the device straight lines, in particular pyramid straight lines.

The position of each of the straight line forming points thus in particular matches either the position of one of the x-ray markers (in particular, the position of the geometric centre point of the x-ray marker) or the position of one of the device intersection points.

The device straight lines, in particular the pyramid straight lines, defined by the arrangement preferably do not all lie in one plane but rather in particular in at least two planes.

The arrangement in accordance with the invention substantially facilitates an assignment between the x-ray markers and the image markers in an x-ray image. Since the x-ray markers lie on device straight lines which are invariant when imaged, it is possible to search in the x-ray image for corresponding straight lines (for example by means of an algorithm) which are formed by image marker candidates (i.e. possible image markers). Since at least six straight line forming points, in particular at least six x-ray markers, preferably lie on device straight lines, they can be used for an algorithm which also uses the pinhole camera principles (see above) and which calculates the imaging geometry data which in particular describes the geometry of the projective image. Since the x-ray markers lie on the device straight lines, it is more easily possible to find the correct assignment for them.

The assignment is further facilitated by the fact that a minimum number of three straight line forming points, which is greater than two (for example three or four or five), preferably lie on at least some of the device straight lines, in particular the pyramid straight lines. This means that even in the case of error-free imaging in the x-ray image, the minimum number of straight line forming points would likewise have to be identifiable in the x-ray image. This reduces the influence of artifacts on the evaluation of the x-ray image, in order to recognize images of the x-ray markers (so-called image markers). If an image marker candidate lies in the x-ray image, and if it is connected to an image marker or to another image marker candidate via a straight line, then this straight line would have to pass through another straight line forming point if the minimum number of straight line forming points is greater than two, in order to confirm that the image marker candidate is an actual image marker. If this is not the case, then the image marker candidate can be excluded from the assignment algorithm as a probable artifact, in particular if all the x-ray markers lie on device straight lines which are defined by a minimum number of straight line forming points which is greater than two.

In accordance with one embodiment, all the x-ray markers lie on pyramid straight lines. The pyramid straight lines intersect in at least one pyramid tip, wherein the number of intersecting pyramid straight lines is known. If the image marker candidates are connected in an x-ray image, the image markers can thus be identified by selecting only the image marker candidates which lie on image straight lines which intersect in an image intersection point with a predetermined characteristic. The predetermined characteristic is that the number of image straight lines which intersect in the image intersection point corresponds to the number of pyramid straight lines which intersect in at least one pyramid tip. The number of pyramid straight lines which intersect in a pyramid tip is predetermined by the x-ray marker device. The condition which an image intersection point through which the image straight lines pass on which the image markers lie has to fulfill is thus known.

The number of straight line forming points, in particular x-ray markers, can be the same for all the device straight lines. This can facilitate the recognition of artifacts. It can however also be different for particular straight lines and can in particular differ from the other device straight lines by two or more straight line forming points (in particular x-ray markers), in order to facilitate the identification and therefore assignment of the straight lines. On the other hand, the risk of reciprocal covering is higher, the more tightly the x-ray markers lie on the device straight lines.

Since straight lines are invariant in projections, it is preferably assumed that the number of straight line forming points is also invariant. The x-ray marker device is preferably configured such that a minimum number of straight line forming points and/or a minimum number of x-ray markers lie on the device straight lines, in particular on the pyramid straight lines. If image straight lines arise from imaging device straight lines, in particular pyramid straight lines, then they have to fulfill the corresponding condition, i.e. there has to be a minimum number of straight line forming point candidates or a minimum number of image marker candidates on the image straight line. Straight line forming points in an x-ray image are image markers or intersection points which correspond to device intersection points, in particular pyramid tips. Due to the aforesaid known minimum number, artifacts can thus be excluded with a high degree of probability.

In practice, this significantly reduces the number of possible assignments and therefore also the computing time. In summary, it holds that: the greater the minimum number of straight line forming points and/or x-ray markers with a device straight line, in particular pyramid straight line, the more reliably ostensible image markers (artifacts) can be identified.

The computing time can be further reduced by grouping the x-ray markers according to device straight lines, in particular pyramid straight lines, and likewise identifying—in the x-ray image—straight lines which have characteristics which correspond to the characteristics of the device straight lines, in particular pyramid straight lines. These straight lines are referred to here as image straight lines. The image straight lines comprise at least one image marker and are preferably likewise defined by a minimum number of straight line forming points which is greater than two (for example three, four or five). Straight line forming points for image straight lines have the corresponding characteristics as do straight line forming points for device straight lines. "Corresponding" means here that image markers correspond to the x-ray markers and "image intersection points" correspond to the device intersection points, in particular the pyramid tips. If, in the case of a device straight line, at least two of the straight line forming points are x-ray markers, then correspondingly in the case of the image straight line, at least two of the straight line forming points are image markers. Image intersection points can also represent straight line forming points for image straight lines, wherein image intersection points have the same characteristics as the device intersection points, wherein the image straight lines correspond to the device straight lines. If, for example, device intersection points—in particular pyramid tips—fulfill the condition that a particular number of device straight lines, in particular pyramid straight lines, intersect in them, then the corresponding image intersection points fulfill the condition that the same number of image straight lines intersect in them, if no artifacts interfere. If a minimum number and/or maximum number is predetermined for the number of device straight lines (in particular pyramid straight lines) which intersect in the device intersection points (in particular pyramid tips), then the image intersection points fulfill the corresponding condition, if no artifacts interfere. In the image intersection points, the number of intersecting image straight lines should thus be greater than or equal to the minimum number and/or smaller than or equal to the maximum number. If deviations are determined, this can be assessed as an indication that an intersection point in the image is not an image intersection point (or that artifacts are causing said deviation).

In accordance with one embodiment, the straight lines in the image which fulfill the characteristics of the pyramid straight lines are selected as image straight lines. If, for the pyramid tips, a minimum number and/or maximum number has been predetermined for the number of pyramid straight lines which intersect in the pyramid tip, then the intersection points in the image are checked as to whether the known minimum number and/or maximum number of straight lines intersect in them. Only if they fulfill this condition are they selected for subsequent method steps as image straight lines which correspond to pyramid straight lines. The intersection points are correspondingly only selected for subsequent method steps as image intersection points if they correspond to pyramid tips.

The aforesaid minimum number and maximum number can be predetermined by the x-ray marker device. Thus, the minimum number can correspond to the minimum number of pyramid straight lines which intersect in one of the pyramid tips, and the maximum number can correspond to the maximum number of pyramid straight lines which intersect in one of the pyramid tips. The number of straight lines which respectively intersect in the pyramid tips can in particular be the same for all the pyramid tips. In this case, there is for example only one predetermined number. In the method in accordance with the invention, however, the aforesaid minimum number or maximum number can also be used to exclude artifacts as far as possible. Connecting the image markers or image marker candidates in an x-ray image results in a multitude of random intersection points in which, however, only two straight lines typically intersect. If the minimum number for selecting the image intersection points is set so as to be greater than two (in particular greater than three), then it is therefore possible to avoid an incorrect selection of an image intersection point with a high degree of probability. A maximum number can also be defined so as not to confuse image intersection points which correspond to pyramid tips with image markers which do not lie on a pyramid tip but in which a number of straight lines intersect. This maximum number is in particular smaller than the number of x-ray markers minus 1 and corresponds for example to the maximum number of pyramid straight lines which intersect in a pyramid tip or lies between this maximum number and the number of x-ray markers minus 1. The reason for the maximum number which is used in identifying is that typically, fewer straight lines intersect in image intersection points which correspond to pyramid tips than in image intersection points which match image markers which correspond to x-ray markers which do not lie on a pyramid tip.

In the method in accordance with the invention, the minimum number and/or maximum number can thus be used by selecting an intersection point as an image intersection point only if it fulfils the following condition: the number of intersecting image straight lines is greater than or equal to (the minimum number−X) and/or is smaller than or equal to (the maximum number+Y), wherein the minimum number corresponds to the lowest number of pyramid straight lines which intersect in a pyramid tip, and the maximum number corresponds to the greatest number of straight lines which intersect in a pyramid tip, and wherein X and Y are whole numbers greater than or equal to zero. X>0 and Y>0 thus allow artifacts to be tolerated to a certain extent and thus allow the image to be evaluated even if artifacts happen to generate another image straight line which passes through an image intersection point, or if image markers are missing in the image, such that an image straight line is missing in the image intersection point.

If the minimum number is greater than two and more than two image straight lines intersect in an intersection point in the image, then this is already an indication that the intersection point is an image intersection point, since only two straight lines typically intersect at intersection points at which no image markers are situated. In accordance with one embodiment, it is thus in particular possible to subject image intersection points to the condition that a minimum number of image straight lines intersect in them, wherein the minimum number is at least three.

The image markers can be grouped according to image straight lines which have been selected in the image, in particular as described above, i.e. which correspond to device straight lines and in particular pyramid straight lines. The possible assignments can then be determined in groups between x-ray markers which lie on device straight lines (in particular pyramid straight lines) and image markers which lie on image straight lines. This significantly reduces the computational power required. This is also explained further below in connection with the description of the method in accordance with the invention.

The arrangement of the x-ray markers is preferably such that they define at least three device straight lines. Preferably, at least three of the at least three device straight lines intersect in the same device intersection point, i.e. there is a common device intersection point for three or more device straight lines, such that for example three of four device straight lines intersect in the common device intersection point.

Preferably, at least some of the x-ray markers, preferably at least six, lie at the corners of at least one truncated pyramid. The truncated pyramid preferably has at least three side faces, preferably four or five side faces, or more. The number of side faces of the truncated pyramid lies for example between three and ten, for example between three and six. The number of side faces is for example four. The latter means that the truncated pyramid is similar but not identical to the geometry of a cube, which is preferred. Preferably, at least some of the x-ray markers lie at the corners of the truncated pyramid and thus on pyramid straight lines.

In accordance with the present invention, the x-ray markers can thus define arrangements which comprise a pyramid structure, such as for example a truncated pyramid, or a pyramid. The x-ray markers can also lie on the tips of pyramids. In accordance with a preferred embodiment, however, the pyramid tip is—as mentioned—a straight line forming point on which no x-ray marker is situated.

Preferably, the device straight lines intersect in the device intersection point at an angle other than 90°, in order to reduce the risk of covering in the x-ray image. The angle can be obtuse, but is preferably acute, in order to keep as low as possible the variation in the distance between the nearest and furthest x-ray marker, which lie in a predetermined volume which is to be irradiated with x-ray beams, independently of the direction of view onto the x-ray marker device. The acute angle is smaller than 90° and preferably smaller than 80°, 70°, 60°, 50°, 40° or 30°. The x-ray markers can in particular and preferably lie at the corners and/or on the edges of the truncated pyramid, or also on the side faces and/or base areas of the pyramid.

If the device straight lines define device intersection points, then the device intersection points—in particular pyramid tips—preferably lie outside a region which is delineated by x-ray markers. This preferably applies at least to a majority of the device intersection points, in particular pyramid tips. This has the advantage that points outside the x-ray marker region can also be used to determine the possible assignments. X-ray markers preferably lie within the radiation range of the x-ray apparatus which is imaged onto the x-ray image in order to be able to assist in determining the assignments. The device intersection points need not, however, necessarily lie within this radiation range if they are virtual. Thus, by arranging the device intersection points outside the x-ray marker region, it is possible to increase the number of points for which a possible assignment can be found, without packing the x-ray markers more tightly. Packing the x-ray markers more tightly would increase the risk of reciprocal covering, which makes evaluating the x-ray image more difficult. On the other hand, a higher number of straight line forming points facilitates the exclusion and recognition of artifacts.

The x-ray marker device can be used for registering and for calibrating. In accordance with a preferred embodiment, the x-ray marker device is a component of a registration body which allows an object to be registered in a reference system of a navigation system. The object is in particular registered in a reference system in which the x-ray image lies and/or in which a body structure of a patient which is imaged in the x-ray image lies.

In accordance with another embodiment, the x-ray marker device can also be used to determine calibration information for an x-ray apparatus. In particular, the x-ray marker device in accordance with the invention can be used in accordance with the invention to determine said calibration information. This calibration information comprises information concerning the positional relationship and/or spatial relationship between a reference system in which the x-ray apparatus lies and—in the case of a three-dimensional x-ray scan—a 3D scan reference system in which a model of a body, ascertained from the 3D x-ray scan data, lies (see EP 08 156 293.6).

The x-ray marker device in accordance with the invention preferably comprises a navigation marker device and is in particular designed as a registration body. A navigation marker device comprises an arrangement of navigation markers. Navigation markers are markers which can be detected by the detection device of a navigation system. Navigation markers can be active or passive markers which emit or reflect beams and/or waves. The beams or waves can be electromagnetic beams or waves such as for example light or infrared light. They can also for example be sound waves such as ultrasound waves. By detecting the navigation markers, the navigation system can determine the position of the navigation markers. Since the relative position between navigation markers is preferably known, the navigation marker device can be identified. The relative position between the navigation markers and the x-ray markers is also preferably known, such that the position of the x-ray markers can be deduced from the detected position of the navigation markers. Using the method in accordance with the invention, it is possible to determine the relative position of the x-ray imaging geometry relative to the x-ray markers. The position of the x-ray imaging geometry is thus also known to the navigation system if the navigation markers are detected. If an object, for example an instrument or implant, is then used, to which navigation markers are likewise attached whose position relative to the object is known, the navigation system can calculate the position of the object relative to the x-ray imaging geometry. In particular, the system can calculate (with the aid of the imaging geometry data) the position which the object (for example, the instrument) would assume in the x-ray image if it were irradiated with x-ray beams which follow the conditions predetermined by the x-ray imaging geometry. It is thus possible, without activating or using the x-ray device, to virtually calculate the position which the object assumes in the x-ray image. The navigation markers are preferably arranged at a distance from the x-ray markers. The minimum distance between (any) one of the navigation markers and (any) one of the x-ray markers is preferably greater than the minimum distance between the x-ray markers themselves, and in particular greater than the maximum distance between the x-ray markers.

In accordance with one embodiment, the navigation system is informed as to where the image intensifier, i.e. the image plane of the x-ray apparatus, at least approximately lies. This can for example be achieved by attaching navigation markers to the x-ray apparatus, in particular to the image intensifier and/or to the x-ray source. It is also possible by means of a pointer to specify the direction from the x-ray source to the image intensifier to an operator in a way which the navigation system can recognize. The detected navigation markers of the x-ray marker device can then be used in order to at least roughly determine the position of the x-ray marker device relative to the source and the image intensifier. This roughly determined position can then be used in order to use an intelligent choice of initial assignment at the beginning of the assignment method. In particular, it is thus possible to determine which image intersection points correspond to which pyramid tips with the greatest degree of probability. It is then possible to begin the assignment method using a probable assignment between image intersection points and pyramid tips which has been determined in this way. It is thus possible to increase the degree of probability that the assignment method finds the correct assignment more quickly.

The x-ray marker device in accordance with the invention is preferably freely movable (in all directions) relative to the x-ray apparatus, i.e. in particular not attached or fixed stationary relative to the x-ray apparatus, and is not restricted in its degrees of freedom. In particular, it preferably does not have to be attached or fixed to the x-ray apparatus. This facilitates handling it. This in particular reduces the expenditure in time as compared to conventional registration kits. Since it is preferably freely movable and not fixed, the x-ray marker device in accordance with the invention can also be more easily sterilized. The mechanics of the x-ray apparatus are also not burdened by the x-ray marker device in accordance with the invention which is preferably not fixed to the x-ray apparatus. Advantageously, sterile coverings do not have to be placed around the x-ray marker device in accordance with the invention, since a complete sterilization is possible due to its free mobility. In particular, the quality of the x-ray image is thus not impaired by a sterile covering.

The present invention advantageously helps in particular in the following challenges: firstly, as many image markers as possible are preferably identified in the x-ray image, wherein it is in particular assumed that the markers of a rectifying grid, if provided, have already been removed. Secondly, artifacts are preferably recognized, i.e. it should preferably be correctly recognized that an image marker candidate is an artifact or is an image marker. Thirdly, the identified image markers are preferably correctly correlated with (assigned to) the physical markers, i.e. the x-ray markers. The use in accordance with the invention of invariant characteristics helps in solving all three aforesaid challenges. The second and third points can in particular be interwoven.

The present invention also relates to a method for determining an assignment between x-ray markers of an x-ray marker device and image markers of an x-ray image. The invention relates in particular to the use of the x-ray marker device in accordance with the invention in the method in accordance with the invention.

If the correct assignment has been found, then the x-ray beam imaging geometry corresponding to the assignment is also determined, on which imaging the x-ray marker device in order to generate the x-ray image is based and which is described by imaging geometry data. In the case of x-ray imaging, it is assumed that this is projective imaging which in particular follows the laws on which the principles of the pinhole camera are based.

On the basis of a known x-ray beam imaging geometry, it is in particular possible to calculate the position of an x-ray source relative to the x-ray marker device. The calculated position of the x-ray source clearly corresponds to the intersection point in which reversing x-ray beams which generate the x-ray image would intersect. If the projection matrix is known, then it is possible on the basis of this—if, for example, the position of an object relative to this calculated position is known—to calculate the image which this object would produce on an x-ray image generated by the x-ray source. The projection matrix is an example of an imaging matrix which images a three-dimensional point in space (for example, in a global coordinate system) onto a two-dimensional point which lies in a plane for which detection of the beams is assumed. The imaging matrix thus describes the imaging of the x-ray markers onto the x-ray image. In general, the imaging matrix has eleven degrees of freedom. If a pinhole camera model is assumed, as a simplified camera model for describing imaging, then the degrees of freedom can be reduced to ten.

Both matrices (comprising ten or eleven parameters) are projection matrices. The difference in the ten-parameter version is that in this case, the precondition is in particular incurred that the axes of the image sensor are orthogonal to each other. The more general scenario comprising eleven parameters allows shearing between these two axes.

In the method in accordance with the invention, the arrangement of x-ray markers in space is known, wherein this can be the arrangement of all or some of the x-ray markers of the x-ray marker device. Preferably, the arrangement is known of at least the x-ray markers which define invariant characteristics which are retained in projective imaging. The known arrangement preferably comprises at least five, preferably at least six of the x-ray markers which in particular lie on at least two planes and define at least two straight lines. Preferably, the x-ray marker device fulfils the characteristics of the x-ray marker device in accordance with the invention as already mentioned above.

The aim of the method in accordance with the invention is to determine the assignment between x-ray markers and image markers, so as to obtain a precondition for determining the x-ray beam imaging geometry. Thus, when performing the method, the x-ray beam imaging geometry is unknown or is not completely known. It is known with respect to the imaging geometry that it satisfies the conditions of linear imaging, in particular projective imaging (wherein one precondition is in particular that the image does not exhibit any distortions due to the image intensifier. This is the case with C-arms comprising flat-panel detectors; in the case of conventional image intensifiers, a processing step of image rectification is preferably also performed beforehand). The information is not however sufficient to determine the relative position of the x-ray beam source (in particular the calculated x-ray beam source) relative to the x-ray marker device, in particular relative to the arrangement of x-ray markers.

The invariant characteristics which are formed by the arrangement include in particular the invariant straight lines which are formed by the straight line forming points already mentioned above, wherein the straight line forming points which form one of the invariant straight lines preferably—as mentioned—comprise at least one x-ray marker, in particular at least two x-ray markers.

These invariant characteristics are in particular the invariant straight lines already mentioned, i.e. the device straight lines and in particular pyramid straight lines. It also holds in this respect that, if no imaging errors arise, the number of straight lines which intersect in an intersection point remains constant. In particular, it is thus possible to group the straight line forming points, in particular the x-ray markers, according to invariant straight lines. It is however also possible to group them according to intersection points in which the straight lines intersect, i.e. in particular the device intersection points and pyramid tips. It is thus possible to group the straight lines according to intersection points, wherein the straight lines in turn comprise image markers and x-ray markers. Another invariant characteristic is the retention of proximity relationships, i.e. if x-ray markers are adjacent on a device straight line, in particular a pyramid straight line, then this also applies to the image markers corresponding to the x-ray markers on the image straight line corresponding to the device straight line. This also means that a sequence of straight line forming points along a straight line, for example starting from an intersection point of straight lines, is retained. This means in particular that a straight line forming point which is proximate to an intersection point, and another straight line forming point on the same device straight line which is further away from the intersection point, fulfill these conditions both in three-dimensional space with respect to the arrangement of the x-ray markers and in two-dimensional space with respect to the arrangement of the image markers on the image straight line corresponding to the device straight line. If a device marker 1 and a device marker 2 are situated on a straight line, and a device intersection point but no other x-ray markers are situated between the two markers, then an image marker A and an image marker B are shown in the x-ray image which lie on both sides of an image intersection point, wherein it is unclear whether the x-ray marker 1 is to be assigned to the image marker A or B. If, however, the number of x-ray markers differs along a device straight line on both sides of the device intersection point (in particular the pyramid tip), then it is possible to assign the device markers to the image markers. Preferably, the number differs not only by one x-ray marker but by two or more x-ray markers, in order to ensure stability against artifacts. In the embodiment described further below, the number of x-ray markers on one side of the device intersection point is zero, while it is two on the other side of the device intersection point.

Another invariant characteristic is the aforementioned cross-ratio. It is in particular also possible to group the straight line forming points, in particular the x-ray markers and image markers, according to whether they belong to a cross-ratio.

Considered in general terms, the x-ray markers are thus grouped according to at least one invariant characteristic, and the image markers are grouped according to the corresponding at least one invariant characteristic. This grouping in accordance with the invention also in particular comprises the grouping of groups which arise from grouping the x-ray markers and/or image markers according to invariant characteristics. X-ray markers which lie on the same device straight line are for example combined to form a device straight line group, and image markers which lie on a (selected) image straight line are combined to form an image straight line group. One example of this is the straight line groups which can be grouped to form intersection point groups. This grouping in accordance with the invention drastically reduces the number of possible permutations, for a group-for-group assignment between the image markers and the x-ray markers is then performed in accordance with the invention. This group-for-group assignment in particular also comprises assignment between groups (for example, device straight line groups) which are derived from x-ray markers (or groups derived from them) in accordance with the invention (i.e. by taking into account invariant characteristics) and groups (for example, image straight line groups) which are derived from image markers (or groups derived from them) in accordance with the invention. The x-ray markers of a device straight line are for example assigned to the image markers of an image straight line. In particular, this excludes the possibility of the x-ray markers which lie on a (single) straight line being able to be assigned to image markers which lie on (a number of) different straight lines. As already mentioned, grouping drastically reduces the number of possible permutations. Grouping in accordance with the invention thus allows the imaging geometry data to preferably be calculated (or attempted to be calculated) only for possible assignments which result after grouping in accordance with the invention. The grouping process in accordance with the invention is in particular configured such that groups which arise from the elementary components, i.e. from the x-ray markers or the image markers respectively, are combined to form higher-ranking groups. These higher-ranking groups can then in turn be combined to form even higher-ranking groups. In the given example, the x-ray markers are combined to form device straight line groups, and the device straight line groups are combined to form device intersection point groups. Ultimately, the assignment between the x-ray markers and the image markers is then preferably performed such that only the x-ray markers and image markers which are components of the same groups, i.e. of the lowest-ranking group and all the higher-ranking groups which comprise the respectively lower-ranking groups, are assigned to each other. Preferably, possible assignments are correspondingly sorted according to the rank of the group. It is assumed that the number of groups having the highest rank is the lowest. In particular, the number of highest-ranking groups based on x-ray markers is equal to the number of highest-ranking groups based on image markers. Thus, in the cited example, the number of device intersection point groups is in particular equal to the number of image intersection point groups. If the number is not equal, this is preferably assessed as an indication of artifacts. This invariant characteristic of the same number of groups of the same rank which are respectively derived from the x-ray markers and image markers also in particular applies to the lower-ranking groups. Deviations from this invariant characteristic of the same number of same-rank groups are preferably assessed as indications of artifacts. Artifacts can in particular also be identified in this way.

Preferably, all the lowest-ranking device groups and image groups—in the cited example, the device straight line groups and the image straight line groups—are determined in accordance with the invention. The possible assignments are then preferably determined, group for group, for the lowest-ranking groups. When determining the possible assignments, the aforesaid division of the groups into higher-ranking and lower-ranking groups is preferably taken into account. One of the highest-ranking device groups—in the cited example, one of the device intersection point groups—is singled out and assigned to one of the highest-ranking image groups—in the cited example, one of the image intersection point groups. The singled-out highest-ranking device group contains lower-ranking groups—in the cited example, device straight line groups. One of these lower-ranking device groups is again singled out—i.e. in the cited example, one of the device straight line groups—and assigned to one of the lower-ranking image groups—in the cited example, one of the image straight line groups. All the members of the lower-ranking groups (all the device straight line groups) of the singled-out higher-ranking group (the device intersection point group) are permutatively assigned to the respective lower-ranking image group (the image straight line group) of the singled-out higher-ranking image group (the image intersection point group), wherein all the possible permutations are in particular considered, in order to determine all the possible assignments. In certain circumstances, however, the number of possible permutations can also be reduced in this case. If, for example, the possible assignments between the members of a device straight line group and the members of an image straight line group are considered, then it is also possible in this case, when determining the possible assignments, to also determine all the possible permutations of the assignment between the x-ray markers of the device straight line group and the image markers of the assigned image straight line group. As explained in the following, it is however possible—with the aid of taking into account the invariant characteristics—to reduce the number of possible assignments, such that it is lower than the number of possible permutations. If, for example, a device straight line group contains three members, i.e. three x-ray markers, and an assigned image straight line group likewise contains three members, i.e. three image markers, then three factorial possible permutations result, i.e. six possible assignments. Preferably, the possible assignments are determined group for group by taking into account whether an elementary group belongs to a higher-order group and by taking into account the resultant invariant characteristics. The invariant characteristics taken into account include in particular the proximity relationships already mentioned above and/or the cross-ratio. If it is assumed that a device straight line group comprises for example four x-ray markers and that in order to determine the possible assignments, this device straight line group is assigned to an image straight line group which preferably comprises the same number of image markers, i.e. four image markers, then four factorial possible assignments result in principle, i.e. twenty-four possible assignments. By classifying the elementary group, i.e. the device straight line group, into higher-ranking groups, i.e. the intersection point group, it is possible to drastically reduce these possible assignments between elementary groups by taking into account invariant characteristics, as indicated above. Preferably, of the given possible permutations, only those which satisfy these invariant characteristics are selected as possible assignments. Since the device straight line group is a member of a device intersection point group, it is possible to determine, by taking into account the invariant proximity relationships, which of the four markers lies nearest, second-nearest, third-nearest and fourth-nearest (i.e. least nearest) to the intersection point. A corresponding procedure can be performed for the image straight line group. In this case too, the group elements—i.e. the image markers—are sorted according to their proximity to the image intersection point. This then has the result that only one of the twenty-four permutations is selected, for which the x-ray marker nearest to the device intersection point is assigned to the image marker nearest to the image intersection point, the second-nearest x-ray marker is assigned to the second-nearest image marker, the third-nearest x-ray marker is assigned to the third-nearest image marker, and the fourth-nearest x-ray marker is assigned to the fourth-nearest image marker. If there are more x-ray markers, this would be continued correspondingly. Thus, by using the invariant characteristic of the proximity relationship in connection with whether the elementary group belongs to a higher group (which in this case defines the intersection point), it is possible to drastically reduce the number of possible assignments predetermined by the permutations. If, as in the given example, only one possible assignment is selected from the given permutations, then the cross-ratio can optionally also be calculated for this remaining possible assignment, if at least four straight line forming points are given. If the cross-ratio for the selected possible assignment matches at least to a predetermined extent, then the possible assignment is supplied to the next method step. It is also possible to directly transition to the next method step after the possible assignment has been selected, without calculating the cross-ratio. Imaging geometry data is, if possible, calculated for the selected possible assignment in said next method step. If, however, the cross-ratio does not match, then the selected possible assignment can in accordance with one embodiment be excluded from the subsequent method. By excluding possible assignments, it is thus possible to further reduce the computational requirement, for the computational requirement for calculating the imaging geometry data and determining a match between an actual and a virtual x-ray image is in particular significant.

Imaging geometry data is calculated for the remaining, in particular selected possible assignments, wherein said imaging geometry data comprises information concerning the x-ray beam imaging geometry which in particular allows the position of the x-ray source relative to the x-ray marker device to be calculated.

When attempting to calculate the imaging geometry data, on the basis of one of the possible assignments determined in accordance with the invention, an algorithm is preferably used which is already based on the principles of the pinhole camera as mentioned above. Reference is again made in this respect to the citations described above.

If imaging geometry data can be calculated, then virtual x-ray images are preferably calculated with the aid of the imaging geometry data and on the basis of the known arrangement of the x-ray markers, and the virtual x-ray images are compared with the actual x-ray image.

If the comparison reveals a match, at least to a predetermined extent, then it is assumed that the imaging geometry data is correct and thus that the corresponding possible assignment is also correct. A match to a predetermined extent can for example be determined in accordance with a least-square-fit method or the like. A virtual x-ray image and an actual x-ray image (of the same size) can for example be superimposed, and the squared pixel distances between a virtual image marker and the corresponding actual image marker can be determined for each image marker and summed. If the sum is below a predetermined limit, then a sufficient match is assumed; if it is over, then a sufficient match does not obtain. It is thus also possible to assess the different possible assignments and to choose the possible assignment for which the best match obtains. This check can be supplemented and refined by comparing other variables.

When evaluating an x-ray image, the image markers are identified. They are preferably recognized by their shape and/or size and/or blackening density. It may nonetheless occur that image regions which may represent image markers and which are called image marker candidates in the following are not image markers. On the other hand, it may occur that in regions of the image in which an image marker should be visible, it cannot be recognized or cannot be clearly recognized. The method is preferably designed to determine, on the basis of the known arrangement and in particular its invariant characteristics, whether an image marker candidate is an image marker or not. The information concerning the known arrangement in particular comprises information concerning the number of x-ray markers along the device straight line. This number likewise represents an invariant characteristic, since it is the number on a straight line and straight lines represent an invariant of the projective image. Thus, in accordance with the invention, the invariant characteristics enable image marker candidates to be recognized or rejected as image markers. It is in particular also possible to recognize when an image marker candidate should be recognizable in the image at a particular point, since an image marker is expected at said point but such an image marker candidate is not present. In general, it is thus possible on the basis of the invariant characteristics to recognize artifacts in the image which are in particular missing image marker candidates or image marker candidates which are to be rejected. Preferably, image marker candidates are in particular determined as image markers when they are situated on an image straight line on which a minimum number of image marker candidates are situated. This minimum number is predetermined by the device data. The minimum number is equal to the minimum number of x-ray markers on device straight lines. In accordance with the method, it is preferably assumed that a corresponding minimum number applies to image markers on the image straight line. If, for example, at least three x-ray markers lie on an image straight line, then this correspondingly applies to the image markers. If, for example, four straight line forming points lie on an image straight line, which for example consists of an intersection point which corresponds to a pyramid tip (recognizable by the invariant number of intersecting straight lines) and three image marker candidates, then it is also possible—with the aid of the cross-ratio—to check whether the four image marker candidates are image markers, for the cross-ratio also represents an invariant characteristic which can serve to distinguish correct image marker candidates and image marker candidates which are to be rejected.

If a possible image straight line has been identified in the x-ray image, then it is for example possible to test whether the same number or minimum number of image markers are situated on this possible image straight line as are situated on the corresponding device straight line. In accordance with a preferred embodiment, the number of x-ray markers on the device straight lines is two or more than two, for example three or four or five. The number of straight line forming points is preferably three or more. If a straight line is then recognized in the x-ray image which is formed from an intersection point of straight lines and an image marker candidate, then it is possible in accordance with a preferred embodiment to then define this image marker candidate as an image marker if another image marker candidate is situated on this straight line, i.e. if at least one of the invariant characteristics which can be derived from the device data, i.e. for example the minimum number of straight line forming points on device straight lines and therefore also on image straight lines, is fulfilled. Preferably, image marker candidates are thus recognized as image markers if they are situated on a straight line on which a minimum number of image markers and/or image marker candidates are situated in total. The minimum number is in particular 2, 3, 4 or more. The minimum number corresponds in particular to the minimum number of x-ray markers on device straight lines.

Preferably, image marker candidates are determined as image markers if they are situated on an image straight line which intersects with a predetermined minimum number of other image straight lines. This minimum number is also an invariant characteristic which can be determined from the device data. In this example, such an image straight line comprises at least one straight line forming point which is an image intersection point in which a predetermined minimum number of image straight lines intersect. This minimum number of image straight lines which intersect in the image intersection point is preferably greater than 2 or 3, for example 3, 4 or 5. The straight line forming point is in particular not identical to an image marker. The number of intersecting image straight lines is in particular smaller than that of the minimum number of device straight lines which intersect at the location of an arbitrary x-ray marker. In the example shown in FIG. 3, this is the number of x-ray markers minus 1. This minimum number is also an invariant characteristic and can be used as an upper limit for identifying image intersection points which correspond to pyramid tips. Thus, if the number of straight lines which intersect in an image intersection point is greater than or equal to the given minimum number and smaller than said upper limit, the image intersection point can be correspondingly determined as a pyramid tip.

The invention preferably also relates to a navigation method which comprises one of the aforesaid methods in accordance with the invention for determining an assignment between x-ray markers and marker images. Once it has been determined in accordance with the invention that one of the possible assignments is correct, the imaging geometry data corresponding to the correct possible assignment is used in accordance with the navigation method in accordance with the invention to determine the position of an object in the x-ray image. When determining the position of the object in the (two-dimensional) x-ray image, the three-dimensional position of the object is taken as a basis. To this end, object position data (three-dimensional position data) is preferably provided to the navigation method which describes the position of the object in space. This position data is for example detected with the aid of a detection device which is a component of a navigation system. The object comprises for example a navigation marker device which can be detected by the detection device. If the three-dimensional position of the object is known and the imaging geometry data is known, then sufficient information is given in order to be able to calculate the position of the x-ray source relative to the object. This information thus allows the image of the object in the x-ray image to be calculated. It is thus possible to calculate—virtually and with the aid of data which describes the x-ray image—how the object would be displayed in the x-ray image if it had assumed the position in the x-ray apparatus predetermined by the three-dimensional position data (object position data). In other words, a virtual x-ray image of the object is virtually produced in the same conditions as were the case in actual x-ray imaging. The position of the object in this virtual x-ray image is predetermined by the object position data. In accordance with another embodiment of the navigation method, the virtual x-ray image can be correctly displayed even if the x-ray apparatus has moved relative to the patient since the actual x-ray image was produced. In this other embodiment, a navigation marker device is attached to the patient such that it is preferably stationary relative to at least some of the body structures shown in the x-ray image. The imaging geometry can thus be determined relative to a reference system in which the body structures lie. The imaging geometry data can in particular be determined for this reference system as it was given at the time the actual x-ray image was produced. Thus, even after a movement of the x-ray apparatus relative to the patient, it is possible to calculate how the object would be displayed in the case of a virtual x-ray image (if the x-ray apparatus is not moved virtually). In particular, the virtual shape and/or size and/or position of the object in the virtual x-ray image can be determined and displayed.

In accordance with another embodiment, navigation marker devices can also be attached to the x-ray apparatus, in particular to the unit which contains the x-ray source and to the unit which contains the x-ray detector. It is thus possible to calculate the imaging geometry in a reference system of the navigation system by evaluating the x-ray image in accordance with the method in accordance with the invention, i.e. on the basis of the imaging geometry data and the x-ray marker device position data. It is in particular possible to calculate the position of the x-ray source and the position of an image plane in the reference system and in particular relative to the navigation marker device attached to the x-ray apparatus. This enables virtual x-ray images in which the object is virtually displayed to be calculated, once the imaging geometry data has been determined in accordance with the invention, even without the x-ray marker device in accordance with the invention, for example when examining another body structure by means of the x-ray apparatus.

The present invention also relates to a program which, when it is running on a computer, causes the computer to perform the steps of the method in accordance with the invention, in particular one of the methods and navigation methods described above. The computer in particular comprises a processor and a memory. Interfaces are also in particular provided in order to supply the information necessary for performing the method to the computer as data. This is in particular data concerning the arrangement of the x-ray markers in the x-ray marker device (device data) and data which describes the x-ray image (x-ray image data). If the program performs the navigation method, the object position data and in particular patient data (see below) is also preferably supplied to the computer. The data which describes the arrangement of the x-ray markers in the x-ray marker device is also referred to here as device data. The device data in particular comprises information concerning the relative position of the x-ray marker device, wherein the relative position is predetermined by the arrangement of the x-ray markers in the x-ray marker device.

The x-ray image data at least partially describes the x-ray image. In particular, it describes the position of the marker images and/or possible marker images (marker image candidates) in the x-ray image. The device data thus comprises information concerning the relative position of the x-ray markers, while the x-ray image data comprises information concerning the relative position of the image markers. The relative position of the x-ray markers describes invariant characteristics which are retained in projective x-ray imaging and which are reflected in the relative position of the image markers.

Other data which can be supplied to the computer includes the patient data which describes the position of the body structure imaged in the x-ray image. The patient data is in particular obtained by means of the navigation system which detects a navigation marker device which is connected stationary to the body structure.

The program can be stored in a program memory (for example, a CD or ROM) or can be represented in the form of a signal wave which can in particular be transmitted via the internet and which contains information which represents the program. The invention is also directed to these memories or forms of representation which respectively contain the program.

The invention is also directed to a navigation system which in particular comprises a computer onto which the program is loaded or on which it runs. The computer in particular comprises a processor for performing the method steps and a memory for loading the program. A data input device is provided as an interface for inputting the x-ray image data and the device data into the computer. The navigation system also preferably comprises a detection device for detecting navigation marker devices. A navigation marker device attached to the x-ray marker device is preferably detected. A navigation marker device attached to an (at least one) object is also preferably detected. A navigation marker device attached to a body structure of a patient is in particular also detected. The program which runs on the computer of the navigation system is designed to calculate, on the basis of the detected position of the x-ray marker device and the detected position of the object, how the object would be displayed in the x-ray image if it were irradiated with x-ray beams in accordance with the imaging geometry data, wherein the imaging geometry data corresponds to the assignment which has been determined to be correct. Preferably, navigation marker device data is stored in a memory which contains the position of the different detected navigation marker devices relative to the object to which the navigation marker devices are attached. Thus, by detecting the position of the navigation marker device, it is possible to determine the position of the object. Thus, for example, the relative position between the object and the navigation marker device which is attached to the object is stored. The relative position between the x-ray marker device and the navigation marker device which is attached to the x-ray marker device is also stored. Such data can be stored, as described, or can be supplied to the navigation system, for example via a data interface.

DETAILED DESCRIPTION

Figure 1:
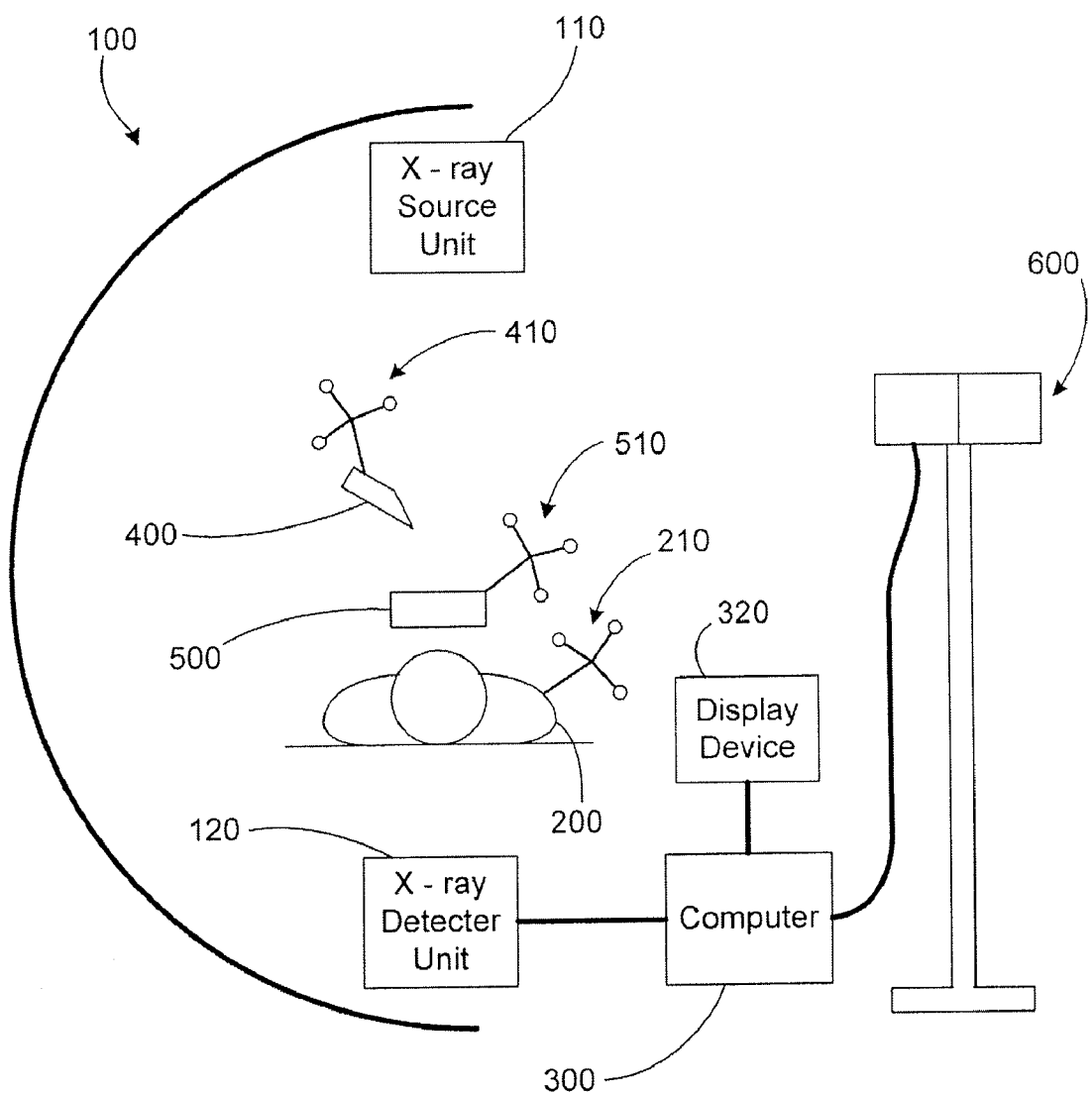
FIG. 1 schematically shows the design of a navigation system in accordance with the invention.

FIG. 1 schematically shows a navigation system in accordance with the invention, comprising an x-ray apparatus 100 (a C-arm) which comprises an x-ray source unit 110 and an x-ray detector unit 120 (for example, an image intensifier). The x-ray light from the x-ray source unit 110 irradiates an object 400 (for example an instrument, in particular a scalpel), the x-ray marker device 500 in accordance with the invention and the patient 200, downwards from above. A navigation marker device 410 is attached to the object 400. A navigation marker device 510 is attached to the x-ray marker device 500. A navigation marker device 210 is attached to the patient 200. The x-ray beams are detected in the x-ray detector unit 120, and the x-ray image generated by the x-ray detector unit 120 is supplied to the computer 300. A display device 320, which is connected to the computer 300, can display image data, in particular for image-guided navigation, or x-ray images, in particular including the virtual x-ray image. Detection signals from the detection device 600 are also supplied to the computer 300. The detection device 600 detects signals from the navigation marker devices 410, 510 and 210, in particular by means of two separate cameras. The detection signals of the detection device 600 are supplied to the computer 300, such that the latter can determine the position of the object 400, the x-ray marker device 500 and the patient 200 using a navigation program. To this end, a database contained in the computer is in particular used, in which the relative position between the navigation marker devices and the objects, i.e. for example parts, in particular surfaces or tips or ends of the object 400, and the relative position between the x-ray markers and the navigation marker device 510 are stored. The positional relationship between the navigation marker device 210 and the body structures of the patient 200 which are visible in the x-ray image is in particular unknown. The navigation system in accordance with the invention in particular allows a display of how the object 400 would be imaged in the x-ray image (in particular its tip), even if the x-ray apparatus 100 is removed from the patient 200 and the x-ray marker device 500 is likewise removed. If the patient 200 does not move after the x-ray image has been generated, then it would be possible to display the object 400 in a virtual x-ray image even without the navigation marker device 210. By using the navigation marker device 210, which is preferably connected stationary to the body structures which are imaged in the x-ray image, it is possible to determine the relative position between the object and the patient even after the patient has moved after the x-ray image has been generated.

Figure 2:
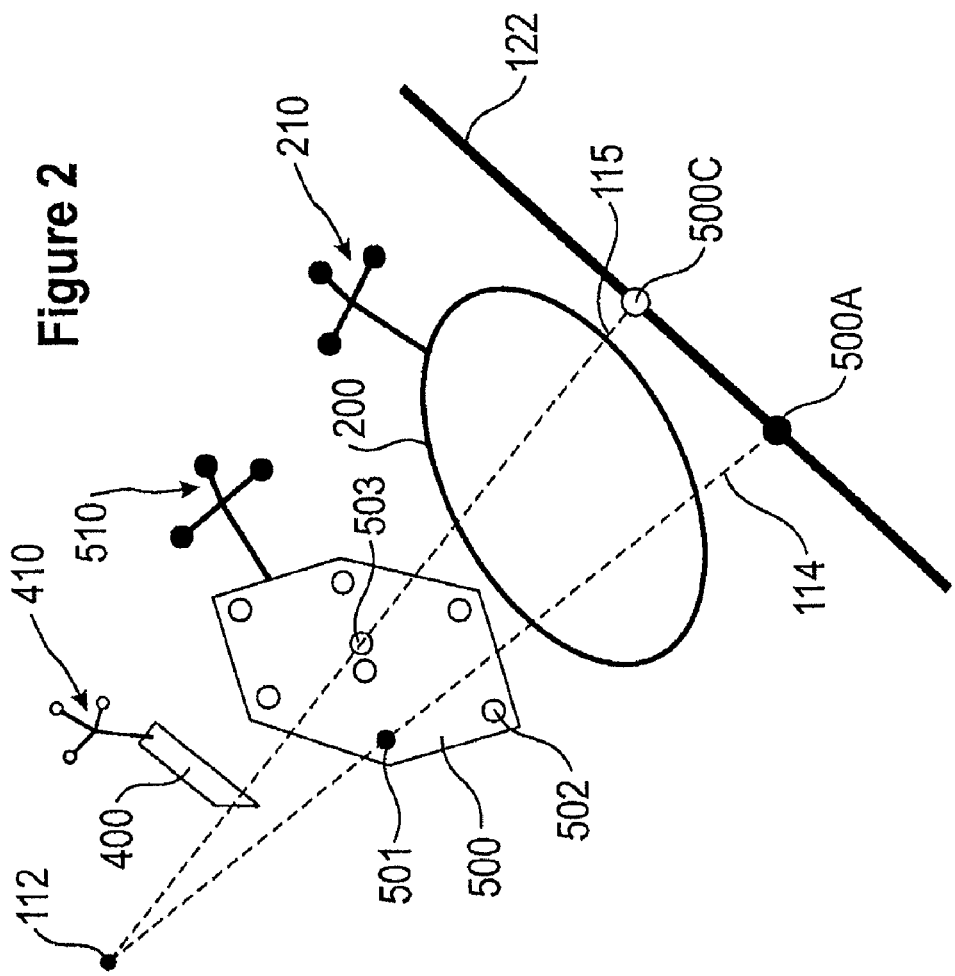
FIG. 2 schematically shows an x-ray marker device being imaged by means of an x-ray apparatus.

FIG. 2 schematically shows x-ray imaging in which an x-ray image is generated by means of x-ray beams which are emitted from a punctiform x-ray source 112 (the position of which can be calculated using the method in accordance with the invention) of the x-ray source unit 110 and hit an x-ray image plane 122 of the x-ray detector unit 120. En route to the x-ray image plane 122, the x-ray beams 114, 115 irradiate the object 400 and the x-ray marker device 500 which comprises x-ray markers 501, 502 shown as circles and other circular x-ray markers which are not provided with reference signs. The x-ray beams then irradiate a body structure 200 of the patient. A navigation marker structure 210 is connected stationary to said body structure. The x-ray marker 501 generates an image marker 500A in an x-ray image which lies in the x-ray image plane 122. Another x-ray marker 503 generates an image marker 500C in the x-ray image. The broken lines 114 and 115 schematically indicate, by way of example, the x-ray beams.

The invention relates in particular to the assignment between image markers, such as for example 500A and 500C, and x-ray markers, such as for example 501 and 503. If it is known which x-ray marker is to be assigned to which image marker, then it is possible to determine from this the position of the punctiform x-ray source 112. If the image marker 500A is assigned to the x-ray marker 501 and the image marker 500C is assigned to the x-ray marker 503, then it is possible to respectively place a straight line through the x-ray marker 501 and the image marker 500A and through the x-ray marker 503 and the image marker 500C. The position of the x-ray markers 501 and 503 can be determined by detecting the navigation marker device 510. The intersection point of these straight lines then matches the position of the punctiform x-ray source.

This is only a description in principle; the mathematical details (algorithms), which also take into account the position of the x-ray image plane 122, in particular the image markers 500A and 500C, relative to the x-ray marker device 500 which is in principle unknown, and which do not necessitate knowledge of this position in order to calculate a virtual x-ray image which would result for the known position of the x-ray source 112 and the image plane 122, are described in the citations relating to the pinhole camera principle as described above. Applying this mathematical detail, in particular algorithms, allows the imaging geometry data—which comprises sufficient information to calculate the virtual x-ray image—to be determined. In this connection, reference is made in particular to the publication by Tsai mentioned above, which describes a specific way of obtaining the calibration of the pinhole camera which is often regarded as a standard. The degree thesis by Yaniv is an example of applying such a calibration to a fluoroscopic system.

If it is assumed that the position of the x-ray source is known, then it is for example possible to calculate which image points the object 400 would generate in the x-ray image. In particular, it is thus possible to calculate where and in what shape and/or size the object 400 would be imaged in the x-ray image. This can in particular be correlated with an image of the body structure 200 in the x-ray image and shown in the virtual x-ray image which superimposes the body structure with the virtual x-ray image of the object.

Figure 3:
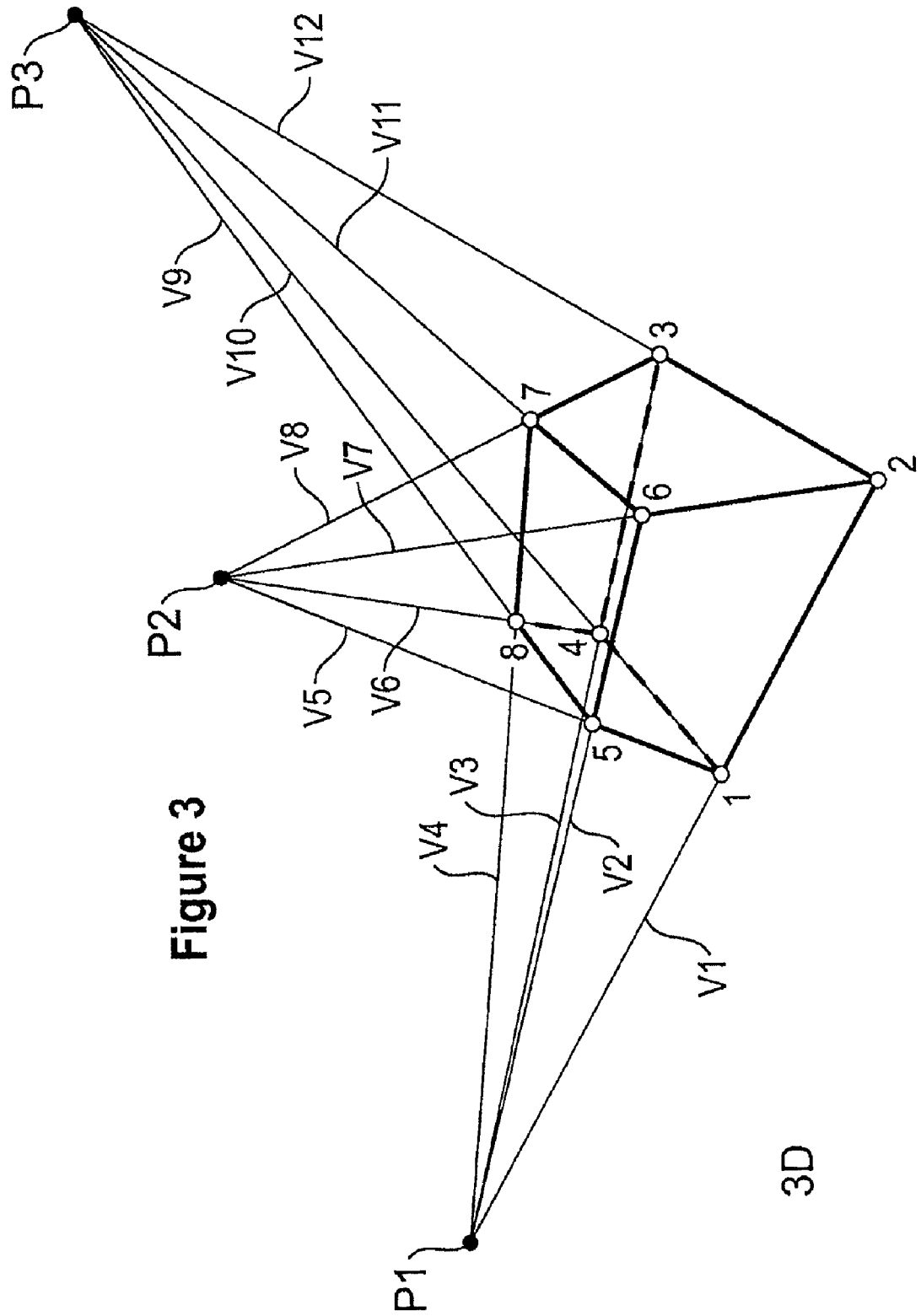
FIG. 3 schematically shows the three-dimensional arrangement of x-ray markers of an x-ray marker device.

As explained above schematically on the basis of FIG. 2, a correct assignment between x-ray markers and image markers is thus essential. Locating a correct assignment becomes easier in accordance with the invention. How this is facilitated in accordance with the invention is explained in the following on the basis of FIG. 3. FIG. 3 shows a possible and preferred arrangement of the x-ray markers of the x-ray marker device.

FIG. 3 schematically shows the three-dimensional arrangement of physical x-ray markers 1 to 8. The x-ray markers 1 to 8 are components of the registration body and have a stationary position with respect to each other. The x-ray markers lie on the side edges of three pyramids which have the tips P1, P2 and P3. The tips P1, P2 and P3 lie in three-dimensional space and are preferably virtual. The x-ray markers 2, 3, 6 and 7 define the base area of the pyramid comprising the tip P1, the x-ray markers 1, 2, 3 and 4 define the base area of the pyramid comprising the tip P2, and the x-ray markers 1, 2, 5 and 6 define the base area of the pyramid comprising the tip P3.

The positions of the x-ray markers are characterized by a number of geometric characteristics. In particular, the x-ray markers lie on side edges and base edges of pyramids. Where it is mentioned here that an x-ray marker or image marker (or its position) lies on a straight line or edge or at a tip or point, this is in particular intended to mean that the geometric centre point of the x-ray marker or image marker fulfils this condition. The pyramids preferably have at least three side faces. In the example shown, there are four side faces. The geometric characteristics facilitate the assignment between the physical x-ray markers 1 to 8 in three-dimensional space and the images of the x-ray markers (in the following, "image markers" for short) in the two-dimensional x-ray image. In particular, it is possible to recognize artifacts and to determine that an image marker corresponding to the physical x-ray marker is missing. The device straight lines V1 to V12 shown in FIG. 3 are all pyramid straight lines. The portions of these pyramid straight lines which form pyramid edges, in particular side edges and/or base edges, are delineated by x-ray markers in the embodiment shown. This is preferred, but not compulsory.

For the x-ray marker 1, for example, the aforesaid geometric characteristics are as follows: the x-ray marker 1 is a component of the base edge (specifically, at a corner of the base edge) of the pyramid comprising the tip P3. The x-ray marker 1 lies on the pyramid straight line V1, i.e. on the pyramid side edge comprising the x-ray marker 2 and the tip P1 as its end points, and the x-ray marker 1 defines a corner point of the base area of the pyramid comprising the tip P2. The x-ray marker 3 has corresponding geometric characteristics, namely those of being a corner of the base area of two pyramids and a component of a pyramid side edge.

The x-ray marker 2 lies at a corner of the base area of all three pyramids (comprising the tips P1, P2 and P3). The x-ray marker 4 lies at a corner of one of the three pyramids (the pyramid comprising the tip P2) and is a component of two side edges of two pyramids, namely the side edge from 1 to P3 and from 3 to P1.

The x-ray marker 8, for example, does not lie at a single corner of a base area of the three pyramids, but is a component of three side edges, namely the side edge from 7 to P1 and from 4 to P2 and from 5 to P3.

In the example shown, the position of each x-ray marker is preferably a component of a pyramid straight line of each of the three pyramids—in the example shown, even of the edges of the pyramids (the side edge and/or base edge). The geometric characteristics, more specifically the pyramid straight lines, which contain edges of the pyramids define imaging-invariant characteristics, namely straight lines which remain invariant in perspective imaging (x-ray imaging), i.e. are imaged onto straight lines again.

Thus, the positions of all the x-ray markers as a whole have multiple geometric and in particular invariant characteristics. In the example shown, they respectively lie on three invariant straight lines which in the subsequent calculation in the algorithm enable an assignment between the (physical, three-dimensional) x-ray markers and the (two-dimensional) image markers. Another invariant characteristic is the proximity relationships of the x-ray markers; thus, the marker 1 is nearer to the pyramid tip P1 than the marker 2, and the marker 5 is nearer to the pyramid tip P2 than the marker 1. Such characteristics, which sort the x-ray markers according to their proximity to the pyramid tips, are likewise retained, i.e. the same sorting according to the proximity to the image intersection points, which correspond to the pyramid tips, results in the image.

Using the invariant characteristics in particular enables the algorithm to be efficiently configured in order to drastically reduce the computing time.

As already stated above, when generating the x-ray image, the x-ray markers are subjected in geometric terms to a projection, as a result of which the two-dimensional image comprising the image markers is generated. The x-ray images can be distorted if image intensifiers having a curved detection area—such as used to be common—were used, or free of distortion if newer flat-panel image intensifiers are used. It is assumed here that distorted x-ray images are rectified in accordance with a common method, i.e. the x-ray image data which is derived from the x-ray images and further processed is preferably free of distortion. As has likewise been mentioned, an essential aspect of the invention is that geometric characteristics of the marker arrangement are utilized which are invariant in a geometric projection, wherein the characteristics which have already been listed above include in particular the fact that straight lines are imaged onto straight lines which are also referred to here as invariant straight lines. As stated above, each of the x-ray markers is preferably arranged at a pyramid corner or on a side edge between a base area corner and the pyramid tip and is thus a component of a pyramid straight line which is defined by three points, or the x-ray marker is arranged at a corner of a pyramid and is thus likewise a component of a pyramid straight line which is defined by the pyramid tip and another x-ray marker between the pyramid tip and the base area corner. Thus, in the example shown, a total of three pyramid straight lines pass through an x-ray marker, wherein the three pyramid straight lines are each defined by another x-ray marker and one of the pyramid tips. Since, as mentioned, straight lines are imaged onto straight lines by a projection, locating image markers—to which physical x-ray markers can be assigned—in the two-dimensional image is facilitated and accelerated.

Figure 4:
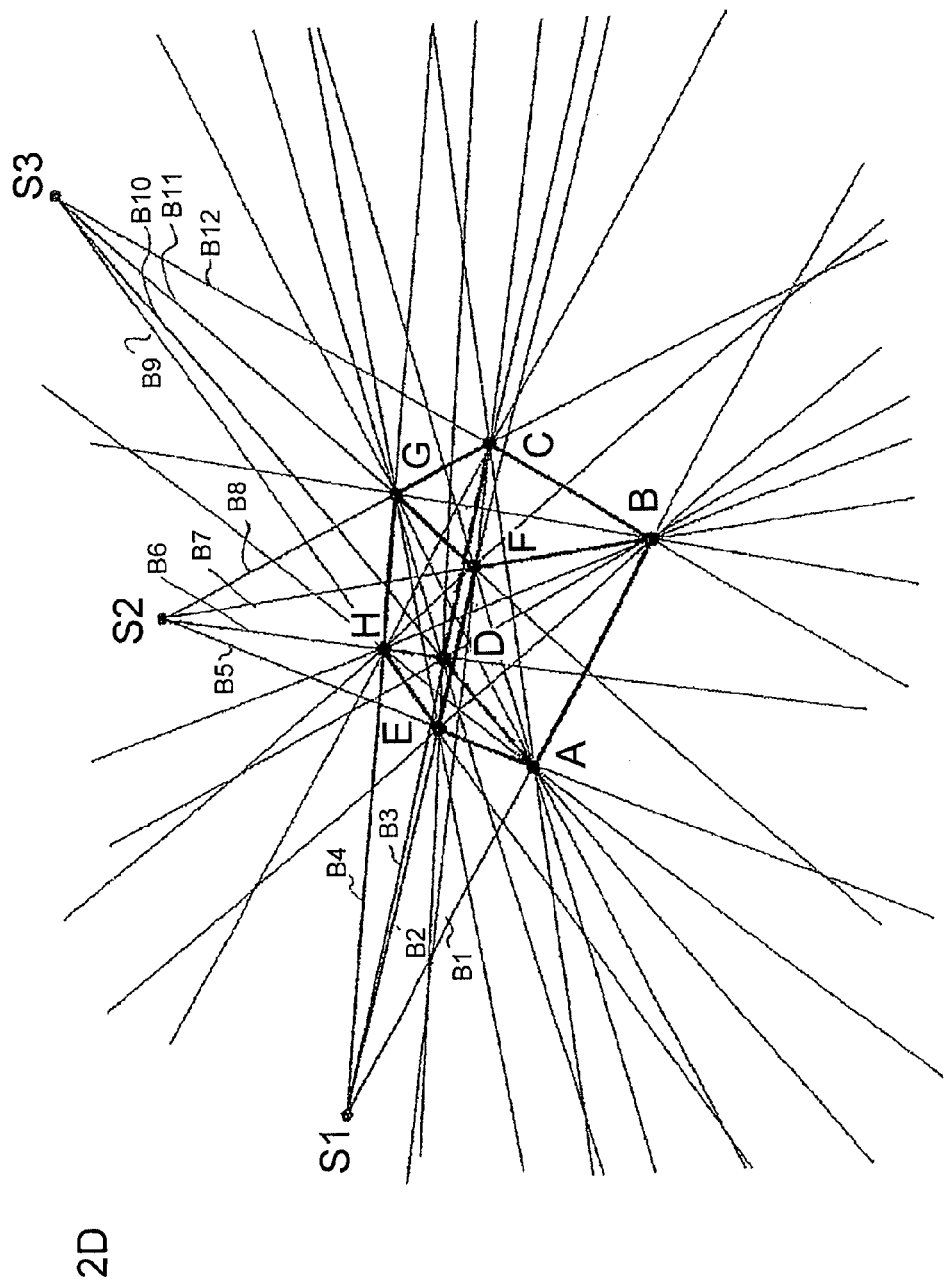
FIG. 4 shows the relative position of image markers in an x-ray image of the x-ray marker device of FIG. 3.

The x-ray markers 1 to 8 can be shown in an x-ray image by image markers A, B, C, D, E, F, G and H. These are shown in FIG. 4 by black circular areas. In accordance with the method in accordance with the invention, it is then to be clarified as to which of the x-ray markers 1 to 8 is to be assigned to which of the image markers A to H. In particular, all the image markers A to H are to this end preferably connected to each other by image straight lines in the two-dimensional x-ray image in accordance with FIG. 4. Seven straight lines (the number of image markers minus 1) thus intersect in each image marker. In addition to these image intersection points, there are also other image intersection points, wherein only two straight lines usually intersect in one point (see FIG. 4). Aside from these image intersection points, however, there are also the intersection points S1, S2 and S3, in which more than two straight lines, more specifically four straight lines, intersect. These image straight lines B1 to B12 correspond to the pyramid straight lines V1 to V12.

Since straight lines are imaged onto straight lines in a geometric projection, intersection points of straight lines are thus also imaged onto intersection points of straight lines. Since four straight lines likewise intersect in each of the pyramid tips P1, P2 and P3, it can be assumed that the image intersection points S1, S2 and S3 are images of the pyramid tips P1, P2 and P3, wherein it is however still unclear as to which pyramid tip P1, P2, P3 is to be assigned to which intersection point S1, S2, S3. The number of straight lines which intersect in the image intersection points thus lies between the minimum number of straight lines which intersect in an image marker (the number of x-ray markers minus 1) and the maximum number of straight lines which randomly intersect in an intersection point (a number typically equal to two, perhaps and very rarely three, depending on the exactness of the image resolution). Correspondingly, the x-ray marker device is preferably configured such that the number of pyramid straight lines which intersect in a pyramid tip fulfill this condition.

The intersection points S1, S2 and S3 which correspond to pyramid tips allow an ordered search for an assignment between the image markers A to H and the physical x-ray markers 1 to 8. The number of possible assignments can be significantly reduced by the knowledge that the intersection points S1, S2 and S3 represent images of the pyramid tips P1, P2 and P3. Without such an ordered search for the correct assignment, on the basis of the geometric characteristics of the arrangement of the physical x-ray markers, in particular by taking into account the projection-invariant geometric characteristics of the arrangement, locating the correct assignment would be significantly more time-consuming. For eight marker spheres, there are eight factorial different possible assignments for which a candidate projection image would have to be calculated and then compared with the actual x-ray image. In the case of eight marker spheres, eight factorial—i.e. 40,320—candidate projection images would thus have to be calculated and compared with the actual image. If artifacts are present in the image, which cannot yet be distinguished from the marker images, the combinatorial effort increases further, since combinations which contain one or more artifacts also have to be considered. This computational requirement can be significantly reduced by the following assignment method described by way of an example.

Figure 5:
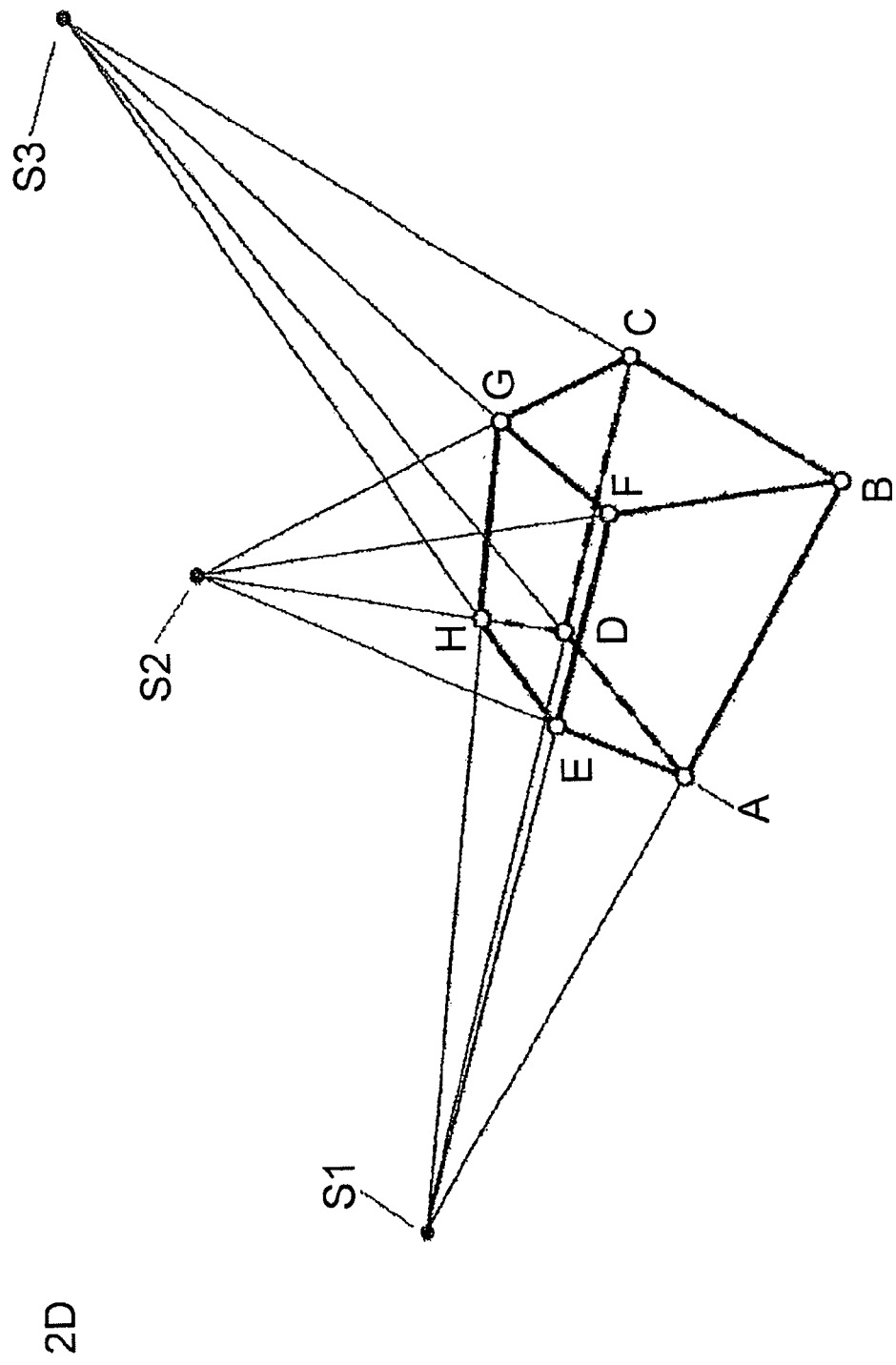
FIG. 5 shows image intersection points which correspond to pyramid tips being determined in the x-ray image.

This utilizes the invariance in perspective images that straight lines are imaged onto straight lines. If, for example, a pyramid tip lies at the intersection point of n straight lines, i.e. has n side edges, then an intersection point of exactly n straight lines results in the x-ray image if all the image markers have been found and there are no artifacts to be considered. If not all the image markers are found which form the straight lines which intersect in the intersection point which corresponds to the pyramid tip, then less than n straight lines can intersect in the intersection point. By imaging straight lines onto straight lines, the proximity relationships between points on straight lines are also retained. Thus, in FIG. 3 for example, the x-ray marker 5 lies between the point P1 and the x-ray marker 6. In the x-ray image, therefore, the image of the x-ray marker 5 (i.e. the image marker 5) likewise lies between the image of the point P1 found by forming intersection points and the image of the x-ray marker 6 (i.e. the image marker 6) on the straight line defined by the image of the point P1 and the image of the x-ray marker 6. In the embodiment described, the pyramid tips exist only by design and not physically. The x-ray marker 4 also lies between the x-ray marker 1 and the point P3. The image of the x-ray marker 4 thus lies between the image of the x-ray marker 1 and the image of the point P3 on the straight line defined by the image of the x-ray marker 1 and the image of the point P3. If this is utilized, then it is possible to perform a procedure as follows:

If the invariant characteristics are utilized, then it is possible to exclude the image straight lines which do not correspond to pyramid straight lines, such that the clearer situation shown in FIG. 5—on the basis of which the subsequent method is explained—results from the situation shown in FIG. 4.

Firstly, it is assumed that the intersection point S1 in the two-dimensional image matches the pyramid tip P1.

S1 is the intersection point of straight lines which are defined by the following image marker pairs: (A, B); (E, F); (H, G); (D, C). In order to use the aforesaid retained proximity relationship, the image marker which is nearest to the intersection point S1 has been cited first in the round brackets above, and then the more distant image marker.

If the situation in FIG. 4 is compared with FIG. 3, and if the assumption made above that the intersection point S1 corresponds to the pyramid tip P1 is followed, then the straight lines defined by the physical markers would be as follows: (1, 2); (5, 6); (8, 7); (4, 3).

In the designation of the straight lines just cited, the physical x-ray marker which is nearest to the point P1 has also been cited first in each case.

In the example aforementioned example, there are a maximum of 4!, i.e. twenty-four, possibilities for assigning one image marker pair from the physical x-ray marker pairs (1, 2); (5, 6); (8, 7); (4, 3) to each of the four image marker pairs (A, B); (E, F); (H, G); (D, C). This may also be described as twenty-four possible bijective images between the quantity of image marker pairs and the quantity of x-ray marker pairs. If, for example, the physical marker pair (5, 6) is assigned to the image marker pair (A, B), then this means that the image marker A is assigned to the physical x-ray marker 5 and the image marker B is assigned to the physical x-ray marker 6. Assigning the marker image A to the physical x-ray marker 6 and the image marker B to the physical x-ray marker 5 is not possible, since—as has been stated above—the proximity relationships are retained. Thus, the first physical x-ray marker of a physical marker pair is respectively assigned to the first image marker of an image marker pair and the second image marker of an image marker pair is assigned to the second physical x-ray marker of a physical marker pair. This significantly restricts the number of possibilities.

The aforesaid permutations of the bijective images between the physical x-ray marker pairs and the image marker pairs respectively represent possible solutions. For each possible solution (bijective image), a mathematical solution to the problem is searched for by means of an algorithm which is based on the known principle of the pinhole camera which has already been mentioned above, i.e. a test is performed as to whether it is possible to calculate, using algorithms, imaging geometry data for the given possible solution which contains information concerning imaging parameters of the camera model, i.e. the external imaging parameters which in particular describe the position and orientation of the radiation source in the global coordinate system (in particular relative to the x-ray markers), and the internal imaging parameters, wherein it may be revealed that no data can be calculated using the algorithm. This then means that the possible solution is incorrect. It may however also be that data can be calculated. It is then possible to check whether this data represents a correct solution. The data contains information concerning the position of the radiation source relative to the three-dimensional arrangement of the x-ray markers and concerning other internal imaging parameters in accordance with the chosen camera model. It thus allows the three-dimensional marker arrangement to be irradiated virtually, so as to virtually generate a two-dimensional image comprising image markers. If the relative position of the virtual image markers in this virtual two-dimensional image matches the relative position of the actual image markers in the actual two-dimensional x-ray image, at least within a predetermined range of error, then an acceptable possible solution has been found. If this is not the case, then the possible solution is to be rejected.

The aforementioned method for checking whether a possible solution (permutation) is correct is performed for all the possible solutions, at least if no correct possible solution is found, or is discontinued if a correct possibility has been found. All the other possible combinations are preferably examined, in order to find an even better possible solution as applicable. The best possible solution is then regarded as the correct assignment. It is possible to expand the assessment of a possible solution which has been found by also considering other typical characteristics of the calculated image, for example particular values or ratios of the internal imaging parameters.

If it has not been possible to find a correct possible solution for the possible permutations in relation to one intersection point (in the given example, the intersection point S1), then the method in accordance with the invention proceeds to the next assumption. In accordance with the next assumption, the intersection point S1 corresponds to the pyramid tip P2.

For this combination, there are the following possible physical marker pairs: (5, 1); (6, 2); (7, 3); (8, 4).

The aforementioned image marker pairs can then be assigned to these physical marker pairs as possible solutions in the way which has already been described above. There are thus again 4!, i.e. twenty-four, possibilities.

If this in turn does not lead to a solution, it is then assumed in the next step that the intersection point S1 corresponds to the pyramid tip P3, and the solution is analogously searched for again for 4!, i.e. twenty-four, possible permutations.

Preferably, the method begins with the intersection point which lies furthest from the image markers in the image plane. In the example shown in FIG. 4, this would be S3. If assigning S3 to P1, P2 and P3 is not successful, the method would then transition to the nearest intersection point S1. The above permutations were explained for this scenario, i.e. it was successively assumed that the intersection point S1 corresponds to the pyramid point P1, P2 and finally P3, as has been described above by way of example. Lastly, a possible solution would be searched for with the aid of S2, by successively assuming that the intersection point S2 corresponds to the pyramid point P1, P2 or P3.

Figure 6:
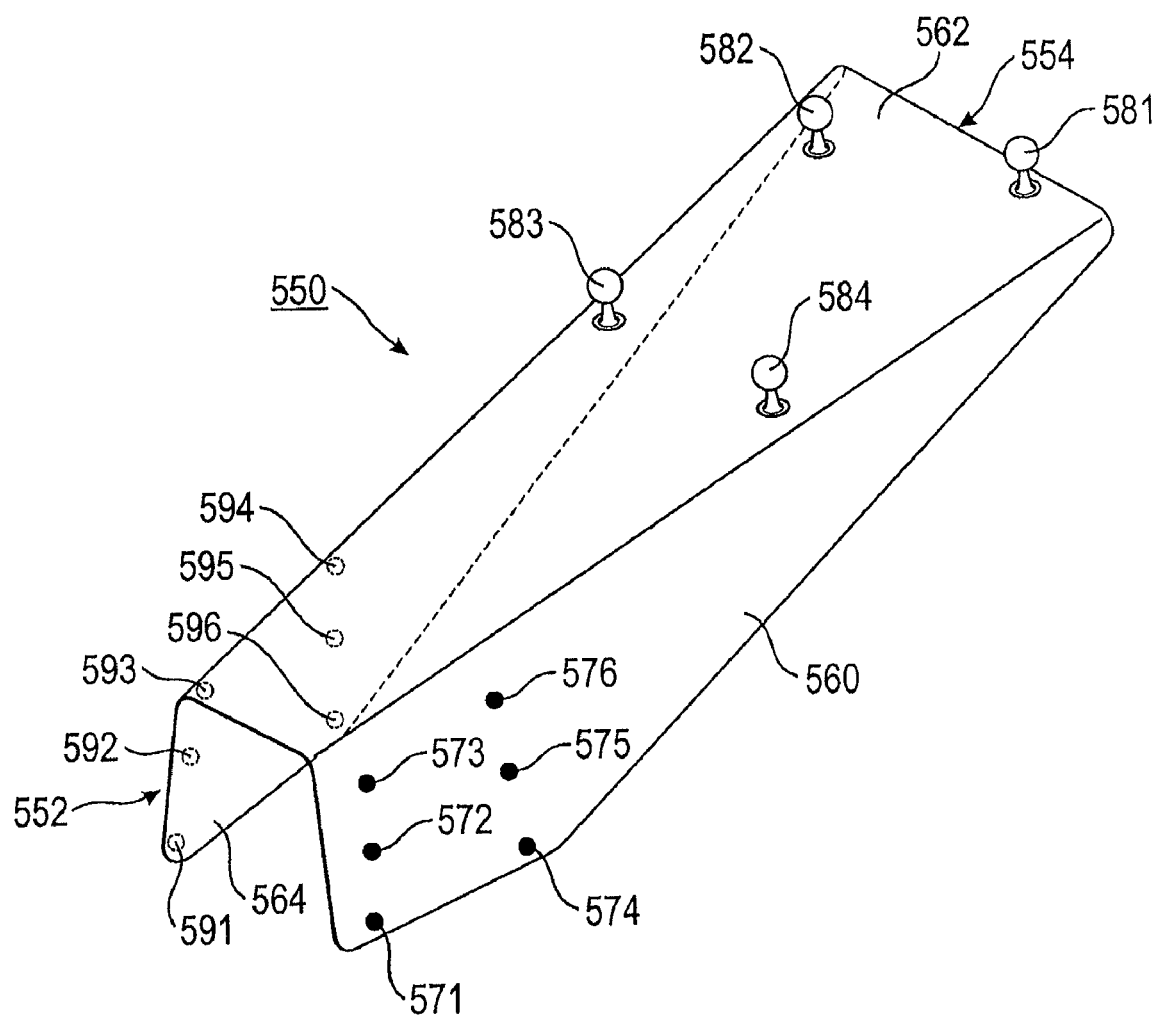
FIG. 6 shows an x-ray marker device in a perspective view.
Figure 7:
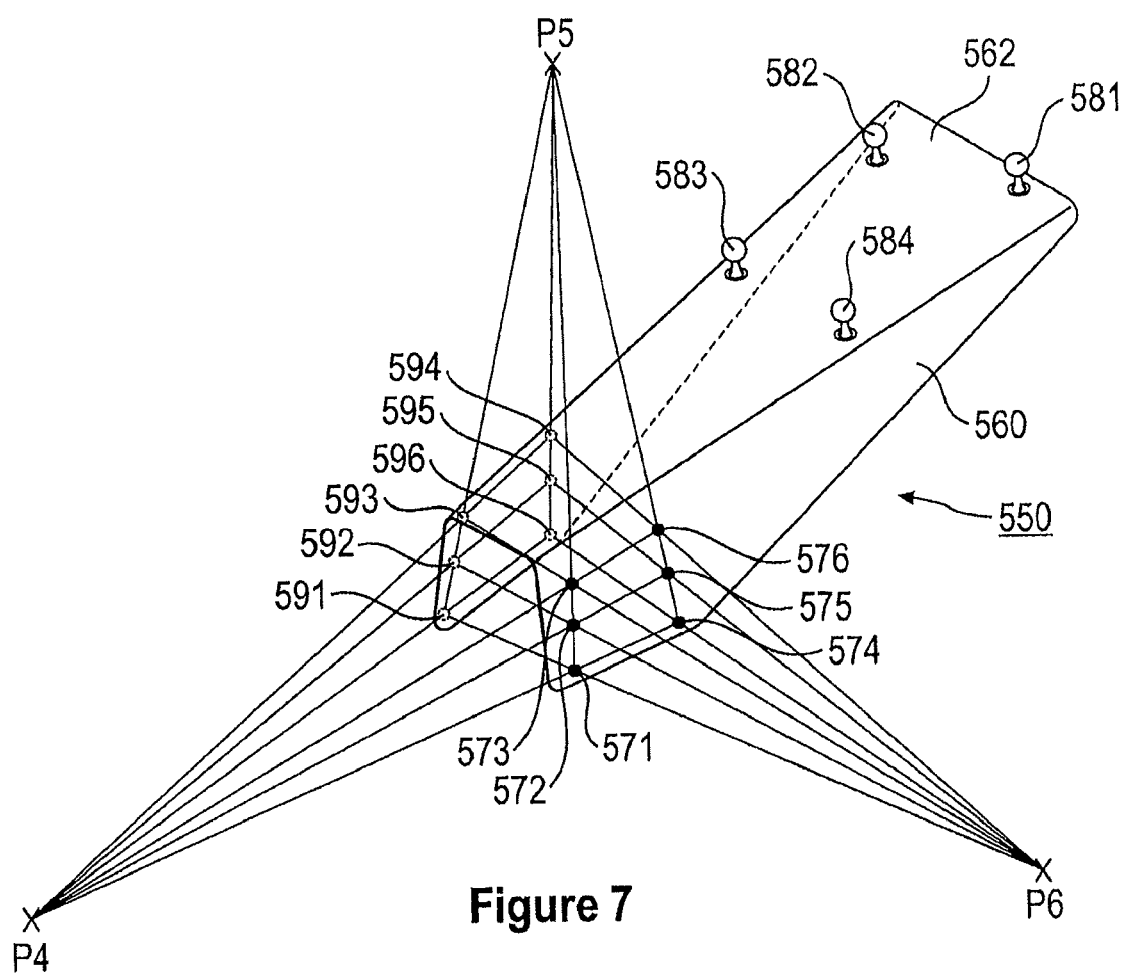
FIG. 7 shows the device intersection points of the x-ray marker device of FIG. 6 which are pyramid tips.
Figure 8:
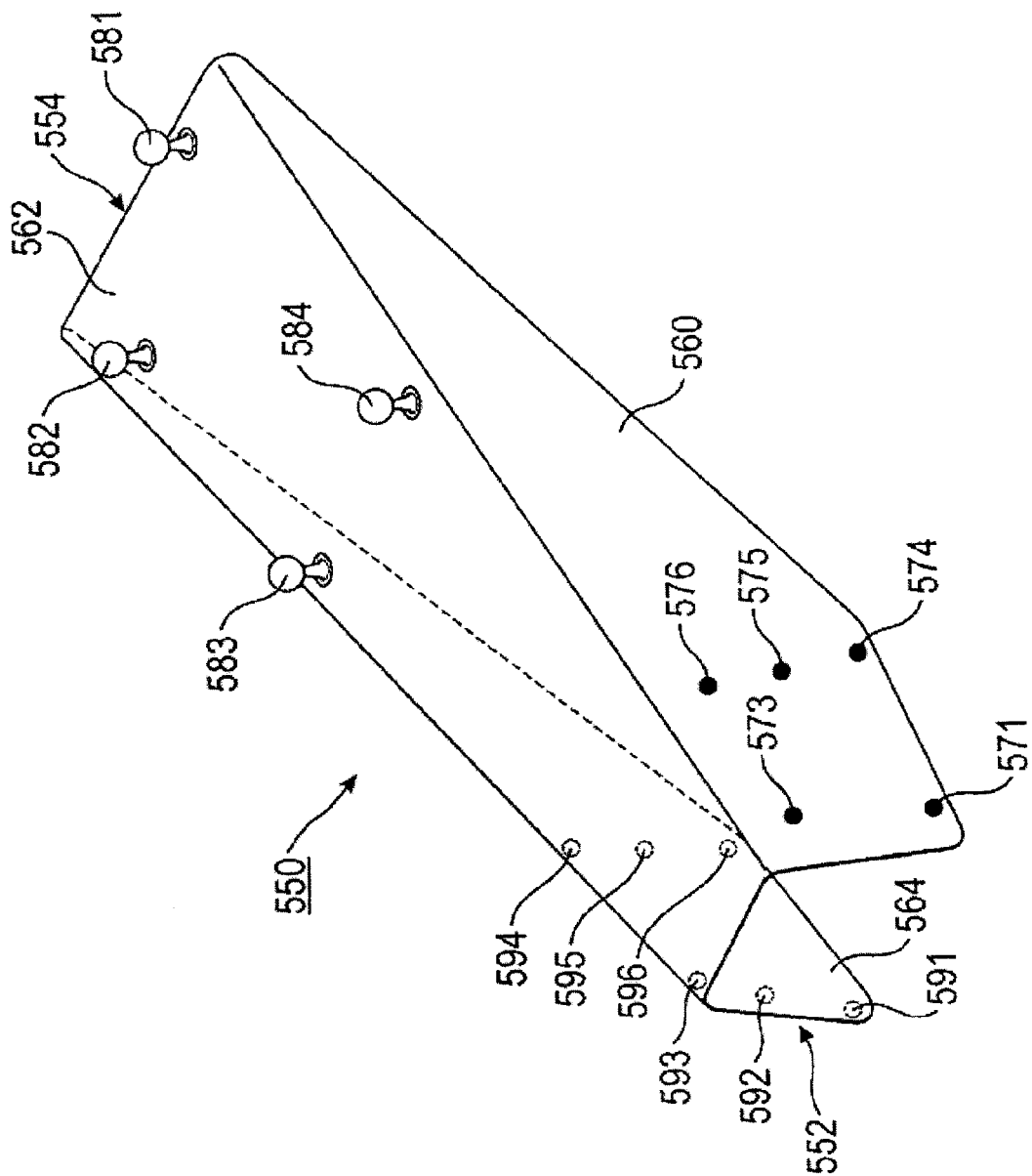
FIG. 8 shows another x-ray marker device in a perspective view.

FIG. 6 shows an embodiment 550 of an x-ray marker device. This embodiment is configured to be elongated and exhibits a U-shaped cross-section which widens from a left-hand end 552 as shown in FIG. 6 to a right-hand end 554. On the right-hand side in the direction of widening is the side wall 560 which represents one arm of the U. In the middle is a middle side wall 562 which lies at the top in FIG. 6, and on the left-hand side is a side wall 564. The left-hand and right-hand side wall diverge further and further from each other, the further away they are from the middle side wall. The x-ray marker device preferably comprises a material which is comparatively permeable to x-ray beams, for example carbon, which serves as a support for the x-ray markers 571, 572, 573, 574, 575 and 576 and for the navigation markers 581, 582, 583 and 584. In particular, the side walls are formed from this material. The x-ray markers are preferably embedded in the side walls which are in particular thin (wall thickness smaller than the diameter of the x-ray markers). The side walls and/or the x-ray markers are in particular optically opaque. The navigation markers 581-584 together form a navigation marker device. In the embodiment shown, the navigation markers are arranged on the middle side wall 562. In the longitudinal direction of the x-ray marker device, they are situated at an end other than the x-ray markers. In these or other embodiments, they are preferably arranged in particular outside a region which is delineated by the x-ray markers. In addition to the x-ray markers 571 to 576 already mentioned, which are supported by the right-hand side wall 560, there are another six corresponding x-ray markers 591-596 which are indicated as dotted circles in FIG. 6. If the middle side wall 562 is divided by a perpendicular plane (not shown), these corresponding six x-ray markers are arranged in the side wall 564, mirror-inverted with respect to said plane. The arrangement of the twelve x-ray markers in total forms a truncated pyramid arrangement similar to the arrangement shown in FIG. 3. The outlying markers of each three markers arranged in a row respectively lie on the side edge of three pyramids. How the pyramids are formed is shown in FIG. 7. The tips of the three pyramids are indicated as P4, P5 and P6. Pyramid straight lines which are formed by the x-ray marker pairs (573, 576), (572, 575), (571, 574), (591, 596), (592, 595) and (593, 594) meet for example in the pyramid tip P4.

Preferably, the side wall (the left-hand, middle or right-hand side wall) is at least partially interrupted, in particular in the region in which the x-ray markers are situated, so as to keep an attenuation of the x-ray beams as low as possible.

The invention described above related by way of example to the scenario in which an image (x-ray image) of a marker device (an x-ray marker device) is generated by means of an imaging device (an x-ray apparatus) which generates an image (an x-ray image) in accordance with the laws of linear imaging. The invention relates in general to the scenario in which a radiation image of a radiation marker device is generated by means of a radiation imaging device which generates a radiation image in accordance with the laws of linear imaging. The radiation imaging device comprises a radiation source (for example an x-ray source or light source) and a radiation detector (for example an x-ray detector or light detector) which detects the radiation image of the radiation marker device. The present invention thus relates in general to the use of any electromagnetic beams such as in particular infrared beams, visible light beams and ultraviolet beams. The present invention thus relates in general to a radiation marker device comprising radiation markers (for example an x-ray marker device or light marker device) which is impermeable to electromagnetic beams of a particular type (for example x-ray beams or light beams) or at least significantly attenuates them. If the radiation marker device relates to visible light, then light markers—i.e. opaque markers (for example spherical)—can for example be supported by a support made of a material which is transparent for said type of electromagnetic radiation (for example glass) and arranged in accordance with the invention. In general terms, the present invention thus relates to the following device:

A radiation marker device comprising an arrangement of radiation markers, wherein the arrangement defines straight lines which are referred to as device straight lines, wherein at least some of the device straight lines, which are referred to as pyramid straight lines, comprise portions which define edges of at least one pyramid.

Correspondingly, the invention relates in general to the following method:

A method for determining an assignment between radiation markers of a radiation marker device and marker images of a radiation image which results from radiation imaging of the radiation marker device with a given imaging geometry, wherein the marker images represent the radiation markers in the radiation image, and wherein in addition to radiation image data, which comprises information concerning the relative position of the marker images in the radiation image, device data is provided which describes the relative position of the radiation markers, and wherein the relative position of the radiation markers describes an arrangement which exhibits invariant characteristics which are retained in radiation imaging and comprise invariant straight lines, wherein the method comprises the following steps:

a) on the basis of the radiation image data and the device data, marker images and radiation markers are respectively grouped by taking into account the invariant characteristics of the arrangement;

b) the possible assignments between marker images and radiation markers are determined in groups;

c) if imaging geometry data for radiation imaging can be calculated for the possible assignments, virtual radiation images are determined on the basis of the calculated imaging geometry data, and the virtual radiation images are compared with the actual radiation image;

d) if a match between a determined virtual radiation image and an actual radiation image to at least a predetermined extent is determined, then the possible assignment on which the determined radiation image is based is recognized as being correct.

In general, the invention also of course relates to a program which, when it is running on a computer, causes the computer to perform the steps of the aforementioned method.

The disclosure described here can in general be interpreted such that the term "x-ray" is replaced by "radiation", wherein the term "radiation" indicates any form of electromagnetic radiation. The radiation image is the image which is generated by said radiation. One example of the radiation image is the x-ray image or an image generated by light.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, "code" or a "computer program" embodied in said medium for use by or in connection with the instruction executing system. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electro-magnetic, infrared or semiconductor system, apparatus, device or medium of propagation, such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiment(s).

Although the invention has been shown and described with respect to one or more particular preferred embodiments, it is clear that equivalent amendments or modifications will occur to the person skilled in the art when reading and interpreting the text and enclosed drawing(s) of this specification. In particular with regard to the various functions performed by the elements (components, assemblies, devices, compositions, etc.) described above, the terms used to describe such elements (including any reference to a "means") are intended, unless expressly indicated otherwise, to correspond to any element which performs the specified function of the element described, i.e. which is functionally equivalent to it, even if it is not structurally equivalent to the disclosed structure which performs the function in the example embodiment(s) illustrated here. Moreover, while a particular feature of the invention may have been described above with respect to only one or some of the embodiments illustrated, such a feature may also be combined with one or more other features of the other embodiments, in any way such as may be desirable or advantageous for any given application of the invention.

What is claimed is:

1. An x-ray marker device comprising an arrangement of x-ray markers, wherein the arrangement defines straight lines which are referred to as device straight lines, wherein at least some of the device straight lines, which are referred to as pyramid straight lines, comprise portions which define edges of three differently oriented pyramids.

2. The x-ray marker device according to claim 1, wherein a total of at least five of the x-ray markers lie on at least three of the pyramid straight lines which intersect in the tip of the at least one pyramid.

3. The x-ray marker device according to claim 1, wherein at least two of the x-ray markers are respectively arranged along at least three of the pyramid straight lines.

4. The x-ray marker device according to claim 1, wherein the number of x-ray markers which respectively lie on pyramid straight lines on both sides of the tip of at least one of the three differently oriented pyramids is different for at least one of the pyramid straight lines than another pyramid straight line.

5. The x-ray marker device according to claim 1, wherein at least one tip of the at least one pyramid lies outside a region which is delineated by the x-ray markers.

6. The x-ray marker device according to claim 1, which comprises a navigation marker device for detecting the position of the x-ray marker device using a navigation system, wherein the navigation marker device lies outside a region which is delineated by the x-ray markers.

7. A method for determining an assignment between x-ray markers of an x-ray marker device and marker images of an x-ray image which results from x-ray imaging of the x-ray marker device with a given imaging geometry, wherein the marker images represent the x-ray markers in the x-ray image, and wherein in addition to x-ray image data, which comprises information concerning the relative position of the marker images in the x-ray image, device data is provided which describes the relative position of the x-ray markers, and wherein the relative position of the x-ray markers describes an arrangement which exhibits invariant characteristics which are retained in x-ray imaging and comprise invariant straight lines, wherein the method comprises the following steps:
   a) grouping marker images and x-ray markers respectively on the basis of the x-ray image data and the device data by taking into account the invariant characteristics of the arrangement;
   b) determining in groups the possible assignments between marker images and x-ray markers;
   c) using a computer to determine virtual x-ray images on the basis of the calculated imaging geometry data, and comparing the virtual x-ray images with the actual x-ray image;
   d) determining if there is a match between a determined virtual x-ray image and an actual x-ray image to at least a predetermined extent, and recognizing as correct the possible assignment on which the determined virtual x-ray image is based if there is a match.

8. The method according to claim 7, wherein the arrangement defines straight lines which have the invariant characteristic and are referred to as device straight lines, wherein the grouping step comprises the step that marker images which lie on a common straight line referred to as an image straight line are respectively combined to form an image straight line group, and x-ray markers which lie on one of the device straight lines are respectively combined to form a device straight line group, wherein in order to determine the possible assignments between the x-ray markers and image markers, a determination is made as to which assignments between the image straight line groups and the device straight line groups are possible.

9. The method according to claim 8, wherein the grouping step comprises the step that device straight line groups which are based on device straight lines which intersect in a common device intersection point are combined to form device intersection point groups, and image straight line groups which are based on image straight lines which intersect in a common image intersection point are combined to form image intersection point groups.

10. The method according to claim 9, wherein the step of determining the possible assignments in groups comprises the step that for each one of the possible assignments between the device intersection points and the image intersection points, x-ray markers which are members of one of the device straight line groups are assigned to the image markers which are members of one of the image straight line groups, such that those x-ray markers and image markers are assigned to each other which respectively assume the same rank in the sequence in a direction along the device straight line starting from the device intersection point in the case of the x-ray markers, and in a direction along the image straight line starting from the image intersection point in the case of the image markers, wherein the number of image markers of the sequence and the number of x-ray markers of the sequence are equal, and wherein the number of x-ray markers on the device straight line, starting from the device intersection point and going in the opposite direction, is different.

11. The method according to claim 7, wherein in the step of determining the possible assignments in groups, invariant characteristics are taken into account such that the number of assignments which are possible due to permutation is thus reduced.

12. The method according to any claim 7, wherein on the basis of at least one of the invariant characteristics of the arrangement determined from the device data, image regions in the x-ray image which may represent image markers are determined as image markers, and/or it is determined that the representation of an image marker is missing in an image region.

13. A navigation method, comprising the method according to claim 7, wherein object position data which describes the position of an object, and x-ray marker device position data which describes the position of the x-ray marker device, is provided, and wherein on the basis of the imaging geometry data which corresponds to the possible assignment which has been recognized as being correct, the x-ray marker device position data and the object position data, the projective image of the object in the x-ray image which corresponds to the imaging geometry data is calculated.

14. A program embodied on a non-transitory computer readable medium comprising computer executable instructions configured to execute the method according to claim 7.

15. A navigation system comprising: a computer on which the program according to claim 14 is loaded or is running, wherein the computer comprises a data input device for inputting the x-ray image data and the device data; a detection device for detecting navigation marker devices in order to determine a position of the x-ray marker device and an object; and a display device, wherein the program is designed to calculate, on the basis of the position of the x-ray marker device and the object that has been determined, how the object would be displayed in the x-ray image if it were irradiated with x-ray beams in accordance with the imaging geometry data which corresponds to the assignment which has been determined to be correct.

* * * * *